(12) United States Patent
Andrisano et al.

(10) Patent No.: US 7,589,219 B2
(45) Date of Patent: Sep. 15, 2009

(54) 2,5-BIS-DIAMINE-[1,4]BENZOQUINONIC DERIVATIVES, USEFUL FOR THE TREATMENT OF ALZHEIMER'S DISEASE, METHOD FOR PREPARING THEM AND INTERMEDIATES OF SAID METHOD

(75) Inventors: Vincenza Andrisano, Bologna (IT); Manuela Bartolini, Mondolfo (IT); Maria Laura Bolognesi, Bologna (IT); Andrea Cavalli, San Lazzaro di Savena (IT); Carlo Melchiorre, Bologna (IT); Maurizio Recanatini, Bologna (IT)

(73) Assignees: Alma Mater Studiorum-Universita' Di Bologna, Bologna (IT); Lay Line Genomics S.p.A., Roma (IT)

( * ) Notice: Subject to any disclaimer, the term of this patent is extended or adjusted under 35 U.S.C. 154(b) by 284 days.

(21) Appl. No.: 10/510,833

(22) PCT Filed: Apr. 11, 2003

(86) PCT No.: PCT/IT03/00227

§ 371 (c)(1),
(2), (4) Date: Jun. 23, 2005

(87) PCT Pub. No.: WO03/087035

PCT Pub. Date: Oct. 23, 2003

(65) Prior Publication Data

US 2005/0261345 A1    Nov. 24, 2005

(30) Foreign Application Priority Data

Apr. 12, 2002  (IT) .......................... BO2002A0198

(51) Int. Cl.
*C07D 307/02* (2006.01)
(52) U.S. Cl. ..................................... 549/472
(58) Field of Classification Search .................. 549/472
See application file for complete search history.

(56) References Cited

U.S. PATENT DOCUMENTS 2,844,585 A    7/1958    Cavallito

FOREIGN PATENT DOCUMENTS

JP    8-193026 A    7/1996
WO    WO-93/20040 A    10/1993

OTHER PUBLICATIONS

Cavallito et al. Journal of the American Chemical society, 1950, 72, pp. 2661-2655.*
Melchorre et al. Journal of Medicinal Chemistry, 1998, 41, 4186-4189.*
Hoppe et al. STN Accession No. 1956:5672, Abstract of Journal of Pharmacology and Experimental Therapeutics, 1955, 155, 106-19.*
Webb, Biochimica Et Biophysica ACTA, vol. 102, pp. 172-184 (1965).
Cavallito et al., Alkyl.Aminodenzoquinones as Curarimimetic Agents, J. Am. Chem. Soc., 72, pp. 2661-2665 (Jun. 1950) (see also attached Abstract, entry 1137 of Merck Index.).
Cutler et al., Prog. Neuro-Psychopharmacol. & Biol. Psychiat., vol. 25, pp. 27-57 (2001).
Melchiorre et al., J. Med. Chem., vol. 41, pp. 4186-4189 (1998).
Patent Abstracts of Japan, vol. 1996, No. 11.

* cited by examiner

*Primary Examiner*—D. Margaret Seaman
*Assistant Examiner*—Nizal S Chandrakumar
(74) *Attorney, Agent, or Firm*—Birch, Stewart, Kolasch & Birch, LLP

(57) ABSTRACT

2,5-bis-diamine-[1,4]benzoquinonic derivatives, having a general formula (I) have proved useful for the treatment of Alzheimer's disease; a method for preparing them and intermediates used in said method are also described.

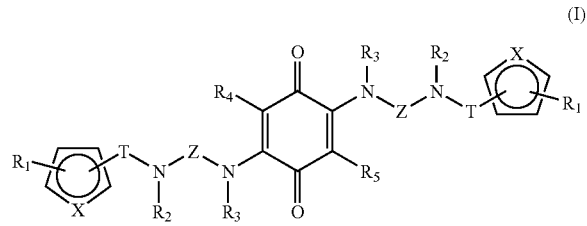

(I)

25 Claims, 6 Drawing Sheets

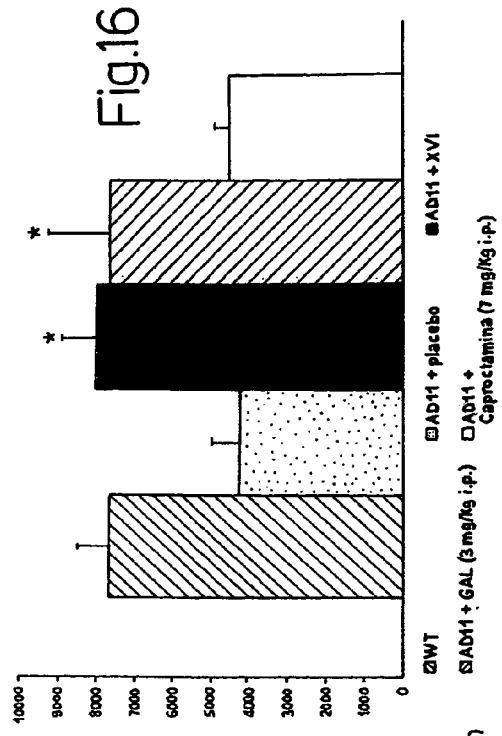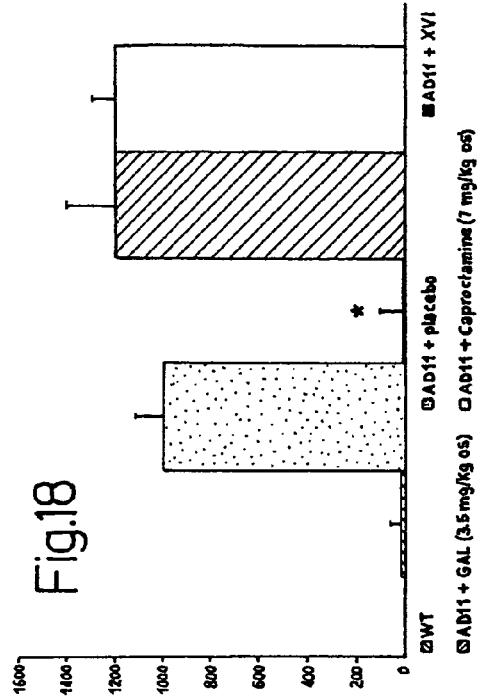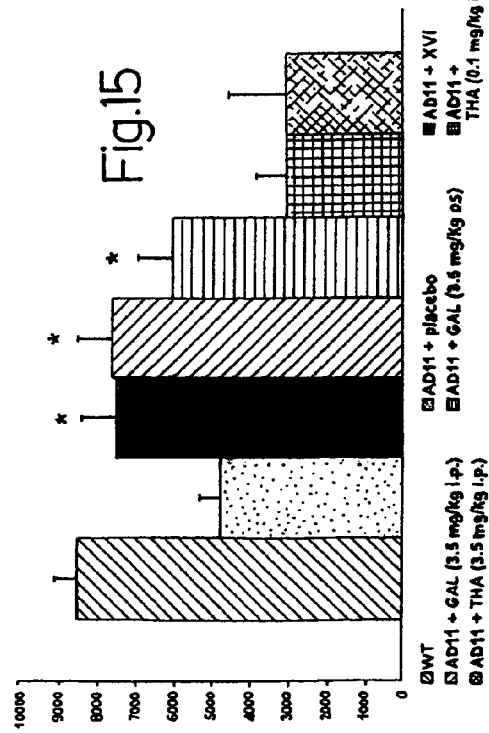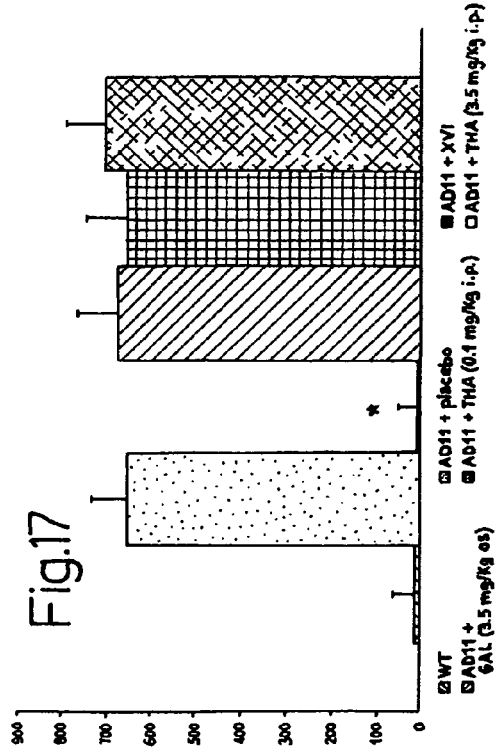

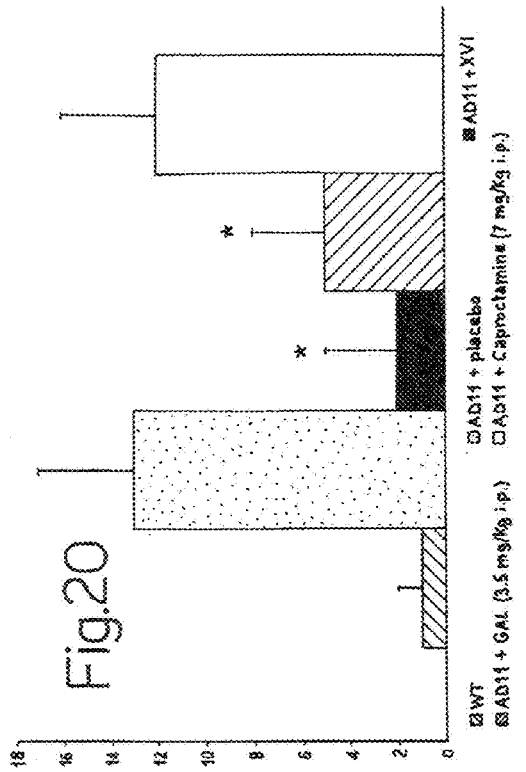
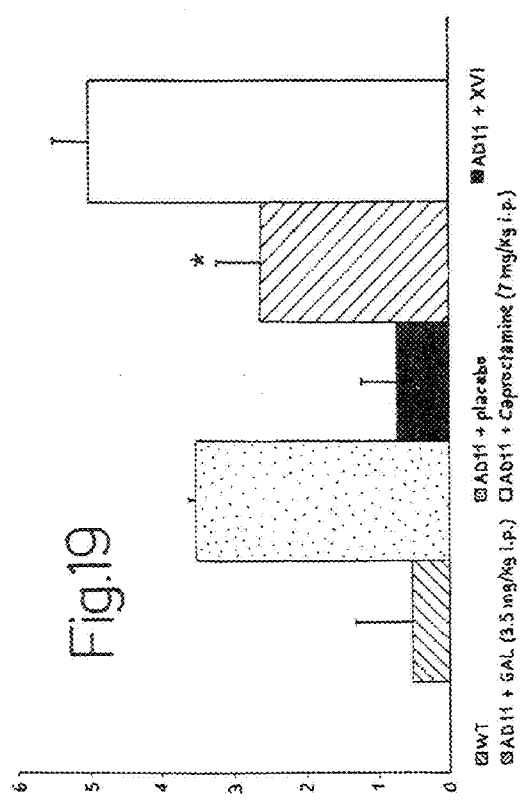
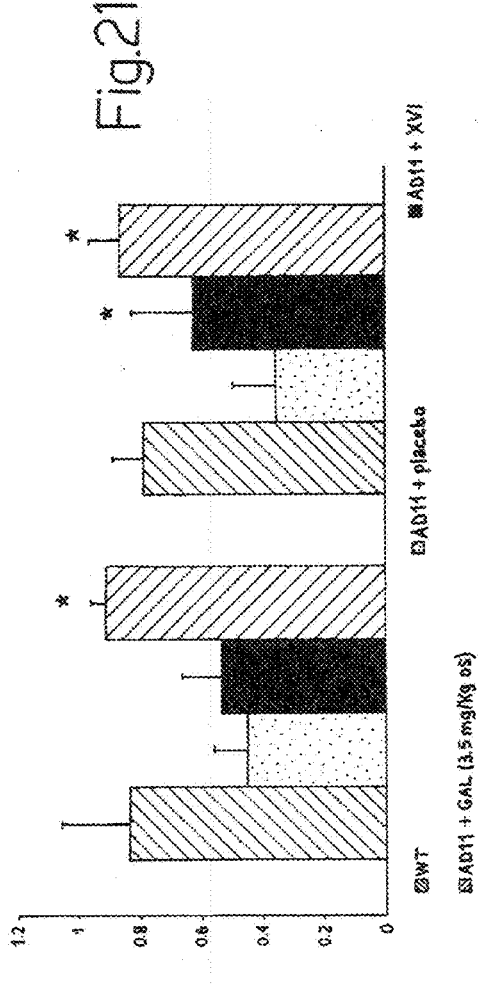

2,5-BIS-DIAMINE-[1,4]BENZOQUINONIC DERIVATIVES, USEFUL FOR THE TREATMENT OF ALZHEIMER'S DISEASE, METHOD FOR PREPARING THEM AND INTERMEDIATES OF SAID METHOD

TECHNICAL FIELD

The present invention concerns new 2,5-bis-diamine-[1,4] benzoquinonic derivatives. The invention also concerns a use of these compounds as medicaments, in particular for the treatment of Alzheimer's disease, their use for the creation of pharmaceutical preparations for the treatment of Alzheimer's disease, pharmaceutical which contain them, methods for preparing them and intermediates of said methods.

The present invention also concerns a use of 2,5-bis-diamine-[1,4]benzoquinonic derivatives for the production of a pharmaceutical preparation having protein β-amyloid (Aβ) anti-aggregating properties and for the treatment of degenerative pathologies of the nervous system.

BACKGROUND ART

Alzheimer's disease (AD) is a neurodegenerative syndrome generally linked with ageing which leads patients to a progressive deterioration of their cognitive and behavioural functions. The great majority of cases of AD has causes that are currently substantially unknown. Also for this reason, today there are still no therapeutic treatments able to halt the progression of the disease, even though some drugs have recently been put on the market, aimed especially at the control of the cognitive symptoms. These drugs—Tacrine (Cognex®), Donepezil (Aricept®) and Rivastigmine (Exelon®)—share the same action mechanism, which consists of the inhibition of acetylcholinesterase (AChE).

The therapeutic approach based on the inhibition of AChe is founded on the observation that the neuron degeneration associated with AD occurs prevalently in cerebral areas innervated by cholinergic neurons. The loss of cholinergic activity in those areas (cortex and hippocampus, especially) would be responsible for the cognitive dysfunctions typical of AD. AChe is the enzyme that inactivates the cholinergic neurotransmitter acetylcholine (ACh), and the hypothesis has been expressed that the block of the functioning of this enzyme could prolong the stimulation of the receptor, strengthening cholinergic transmission. The known drugs mentioned above derive from the application of this hypothesis called "cholinergic hypothesis" (Bartus, R. T.; Dean, R. L., 3rd; Beer, B.; Lippa, A. S. The cholinergic hypothesis of geriatric memory dysfunction. Science 1982, Vol. 217, p. 408-414). However, one cannot overlook the limits of this approach which consist substantially in the lack of action on the progression of the disease and in the presence of undesired collateral effects, which limit dosage and can induce the patient to interrupt taking one of the drugs mentioned above.

Although the strengthening of cholinergic transmission through the inhibition of AchE is a useful approach to the treatment of cognitive symptoms associated with AD, it has recently been proposed that the loss of neurons and the consequent appearance of cognitive symptoms are the result of a cascade of biochemical events linked with the overproduction of β-amyloid protein in certain cerebral areas. This protein tends to aggregate, forming extracellular deposits, which give rise to the typical lesions found in the brain of AD patients: senile plaques. The presence of these plaques produces responses of an inflammatory and oxidative type in the surrounding tissue, triggering a chain of toxic events, including an increase of the phosphorylation of tau protein, due to the activation of enzymes of inflammation and to the formation of oxygenated radical species. The progression of neurodegeneration derives from the impossibility of controlling the spread of these harmful effects. It is therefore necessary to discover pharmacological instruments that are able to act as far upstream as possible in the neurodegenerative cascade. Moreover, it is important to stress that there are other pathologies besides Alzheimer's disease characterised by deposits of Aβ. These pathologies include: Down's syndrome, hereditary cerebral haemorrhage associated with amyloidosis of the "Dutch type", amyloidosis associated with chronic inflammations, amyloidosis associated with multiple myelomas and other dyscrasias of the B lymphoid haematic cells, amyloidosis associated with diabetes type II, amyloidosis associated with diseases deriving from pryons such as Creutzfeldt-Jakob's disease, the Gertsmann-Straussler syndrome, Kuru and scrapie in sheep (WO 02/00603).

From the above it is clear that there is still a considerable need to make medicaments available for the treatment of AD and for the treatment of pathologies characterised by deposits of Aβ.

DISCLOSURE OF INVENTION

The aim of the invention is therefore to provide substances that can be used to advantage in the treatment of AD, of all the other syndromes connected to the accumulation of Aβ, in particular preventing said accumulation, and of the degenerative pathologies of the nervous system.

According to the present invention a 2,5-bis-diamine-[1,4] benzoquinonic derivative is provided having a general formula (I):

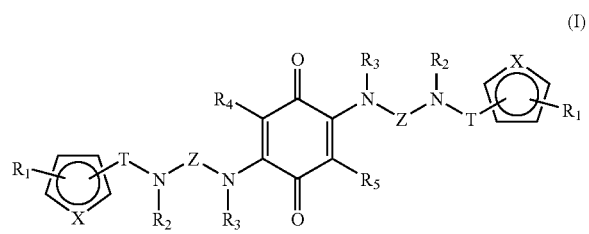

in which $R_1$ represents a substituent chosen from the group consisting of:

a hydrogen, a saturated or unsaturated, linear or ramified alkylic group of from one to five carbon atoms, and a substituent having an attractor electron inductive effect;

$R_2$ and $R_3$, each independently of the other, represent a hydrogen or a saturated or unsaturated, linear or ramified alkylic group presenting from one to five carbon atoms; $R_4$ and $R_5$, each independently of the other, represent a substituent chosen from the group consisting of:

hydrogen, a saturated or unsaturated, linear or ramified alkylic group presenting from one to five carbon atoms, OMe, and SMe;

X represents a radical chosen from the group consisting of:

—HC═CH—,

—HC═N—,

—S—,

—O—, and

—NH—;

T represents a saturated or unsaturated, linear or ramified alkyl group presenting from one to four carbon atoms;

Z represents a saturated or unsaturated, linear or ramified alkyl group presenting from two to thirteen carbon atoms; preferably $R_1$ represents a substituent chosen from the group consisting of:
  a hydrogen,
  a substituent having an attractor electron inductive effect.

Preferably, in the 2,5-bis-diamine-[1,4]benzoquinonic derivative having a general formula (I), $R_1$ represents a substituent chosen from the group consisting of:
  a hydrogen,
  a halogen,
  $NO_2$, and
  MeO;

$R_2$ and $R_3$, each independently of the other, represent a hydrogen or a saturated or unsaturated, linear or ramified alkylic group presenting from one to four carbon atoms; $R_4$ and $R_5$, each independently of the other, represent a substituent chosen from the group consisting of:
  hydrogen,
  a saturated or unsaturated, linear or ramified alkylic group presenting from one to five carbon atoms, X represents a radical chosen from the group consisting of:
  —HC=CH—,
  —HC=N—,
  —S—,
  —O—, and
  —NH—;

T represents a saturated or unsaturated, linear alkyl presenting from one to three carbon atoms;

Z represents a saturated or unsaturated, linear alkyl presenting from two to twelve carbon atoms.

Preferably, in the 2,5-bis-diamine-[1,4]benzoquinonic derivative having a general formula (I), $R_1$ represent a substituent chosen from the group consisting of:
  a hydrogen,
  a halogen,
  MeO;

$R_2$ and $R_3$, each independently of the other, represent a hydrogen or a saturated or unsaturated, linear alkylic group presenting from one to two carbon atoms; $R_4$ and $R_5$, each independently of the other, represent a substituent chosen from the group consisting of:
  hydrogen,
  a saturated linear or ramified alkylic group, presenting from one to four carbon atoms, X represents the radical —HC=CH— or —O—;
T represents the radical —CH$_2$—; and
Z represents a saturated linear alkyl presenting from two to seven carbon atoms.

According to particularly preferred embodiments, in the 2,5-bis-diamine-[1,4]benzoquinonic derivative having a general formula (I) $R_1$ represents a substituent chosen from the group consisting of:
  a hydrogen,
  a halogen,
  MeO;

$R_2$ represents a hydrogen or a saturated linear alkylic group, presenting from one to two carbon atoms; $R_3$ represents a hydrogen; $R_4$ and $R_5$, each independently of the other, represent a substituent chosen from the group consisting of:
  hydrogen,
  a saturated linear alkylic group, presenting from one to two carbon atoms,
  a ramified alkylic group presenting from three to four carbon atoms, X represents the radical —HC=CH— or —O—;
T represents the radical —CH$_2$—; and
Z represents a saturated linear alkyl presenting from two to seven carbon atoms.

Particularly preferred are the embodiments according to which in the 2,5-bis-diamine-[1,4]benzoquinonic derivative having a general formula (I), $R_1$ is in position 2 with respect to T. Preferred are also the embodiments according to which Z represents a saturated linear alkyl presenting from two to seven carbon atoms and the embodiments in which X represents the radical —CH=CH—.

Even more preferred are the embodiments according in which the 2,5-bis-diamine-[1,4]benzoquinonic derivative is chosen from the group consisting of the 2,5-bis-diamine-[1,4]benzoquinonic derivatives illustrated in the enclosed examples.

The 2,5-bis-diamine-[1,4]benzoquinonic derivative having a general formula (I) can exist in different stereoisomer forms such as enantiomer or diastereoisomer. The invention concerns both enantiomers and diastereoisomers or their mixtures. These mixtures can be separated by means of known methods into their stereoisomerically uniform components.

According to the present invention, a 2,5-bis-diamine-[1,4]benzoquinonic derivative having a general formula (I) is provided for use as a medicament.

According to the present invention, a 2,5-bis-diamine-[1,4]benzoquinonic derivative having a general formula (I) is provided for the treatment of Alzheimer's disease in mammals.

According to the present invention, a method is provided for the treatment of Alzheimer's disease in a mammal, comprising the administration to said mammal of an efficacious quantity of a 2,5-bis-diamine-[1,4]benzoquinonic derivative having a general formula (I).

According to the present invention, a pharmaceutical preparation is provided, characterised in that it comprises a 2,5-bis-diamine-[1,4]benzoquinonic derivative having a general formula (I) or one of its pharmaceutically acceptable salts and a pharmaceutically acceptable excipient and/or diluent.

According to the present invention, a use of a 2,5-bis-diamine-[1,4]benzoquinonic derivative having a general formula (I) is provided for the production of a pharmaceutical preparation for the treatment of Alzheimer's disease in mammals.

According to the present invention, there is provided a method for preparing a 2,5-bis-diamine-[1,4]benzoquinonic derivative having a general formula 2 (I); the method comprises a substitution phase, in which on a p-benzoquinone having a general formula (VIII):

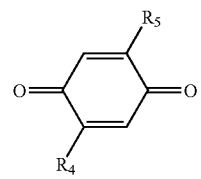

(VIII)

a substitution is carried out with a compound (VII):

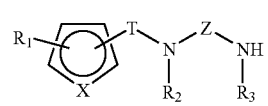

(VII)

in order to obtain the 2,5-bis-diamine-[1,4]benzoquinonic derivative having a general formula (I).

According to the present invention, there are also provided compounds in the group consisting in:

2,5-Bis-{6-[ethyl-(2-methoxy-benzyl)-amino]-hexylamino}-[1,4]benzoquinone, 2,5-Bis-{3-[ethyl-(2-methoxy-benzyl)-amino]-propylamino}-[1,4]benzoquinone, 2,5-Bis-[6-(benzyl-ethyl-amino)-hexylamino]-[1,4]benzoquinone, 2,5-Bis-{6-[ethyl-(3-methoxy-benzyl)-amino]-hexylamino}-[1,4]benzoquinone, 2,5-Bis-{6-[ethyl-(4-methoxy-benzyl)-amino]-hexylamino}-[1,4]benzoquinone, 2,5-Bis-{2-[ethyl-(2-methoxy-benzyl)-amino]-ethylamino}-[1,4]benzoquinone, 2,5-Bis-{7-[ethyl-(2-methoxy-benzyl)-amino]-heptylamino}-[1,4]benzoquinone, 2,5-Bis-{6-[(2-methoxy-benzyl)-methylamino]-hexylamino}-[1,4]-benzoquinone, 2,5-Bis-{6-[ethyl-(2-methoxy-benzyl)-amino]-hexylamino}-3,6-dimethyl-[1,4]-benzoquinone, 2,5-Bis-[6-(2-methoxy-benzylamino)-hexylamino]-[1,4]-benzoquinone, 2,5-Bis-[6-(ethyl-furan-2-ilmethyl-amino)-hexylamino]-[1,4]benzoquinone, 2,5-Bis-{6-[ethyl-(2-nitro-benzyl)-amino]-hexylamino}-[1,4]benzoquinone, 2,5-Bis-{6-[ethyl-(2-chloro-benzyl)-amino]-hexylamino}-[1,4] benzoquinone.

According to a further aspect of the present invention, there is provided the use of a 2,5-bis-diamine-[1,4]benzoquinonic derivative having a general formula (I) for the production of a pharmaceutical preparation for the treatment of pathologies characterised by deposits of β-amyloid protein (Aβ) in mammals.

According to the present invention, there is provided a method for the treatment of the disease of a pathology characterised by deposits of β-amyloid protein (Aβ) in a mammal, comprising the administration to said mammal of an efficacious quantity of a 2,5-bis-diamine-[1,4]benzoquinonic derivative having a general formula (I).

According to a further aspect of the present invention, there is provided the use of a 2,5-bis-diamine-[1,4]benzoquinonic derivative having a general formula (I), for the production of a pharmaceutical preparation for the treatment of degenerative pathologies of the nervous system in mammals.

BRIEF DESCRIPTION OF THE DRAWINGS

The invention will now be described with reference to the enclosed drawings, which illustrate an example of an embodiment without limitation, in which:

FIGS. 12, 13, 14 and 21 illustrate discrimination indices found in experiment;

FIGS. 15 and 16 illustrate the total number of cholinergic neurons found in the basal forebrain;

FIGS. 17 and 18 illustrate the number of neurons that express phospho-tau in the entorhinal cortex;

FIG. 19 illustrates the extracellular charge of APP; and

FIG. 20 illustrate the number of cells accumulated by β-amyloid.

BEST MODE FOR CARRYING OUT THE INVENTION

Figure 1:
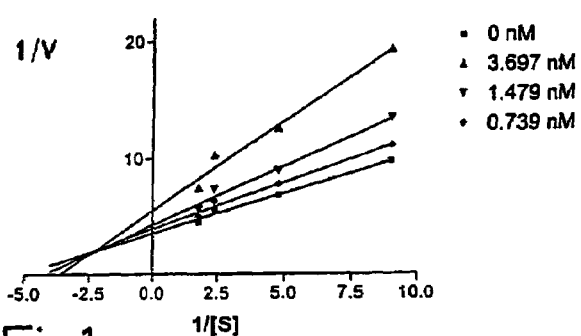
FIG. 1 illustrates an experimental graph of Lineweaver-Burk.

The 2,5-bis-diamine-[1,4]benzoquinonic derivatives represented by the general formula (I) described above can be prepared, for example, starting from a protected (aminoalkyl)-carbamic acid having a general formula (II):

in which D represents a Benzyl (Bn) or another stable protective group in a basic environment. A compound having a general formula (III) is added to the (amino-alkyl)-carbamic acid (II)

in which E represents =O, —Cl, —Br or —I, so as to obtain an intermediate compound having a general formula (IV):

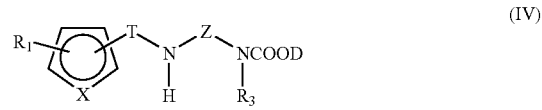

with the condition that, where E represents =O, the reaction occurs in the presence of a suitable reducing agent.

Preferably said reducing agent is $NaBH_4$, the reaction is realised in a protic organic solvent, for example ethanol, at a temperature between 15 and 35° C., in particular at substantially 25° C., in the presence of molecular sieves (in particular of 4 Å).

At this point, the compound (IV) has been made to react in the presence of a base with a compound having a general formula (V):

in which A is an attractor electron group and f is 1 or 2 so as to obtain an intermediate compound having a general formula (VI):

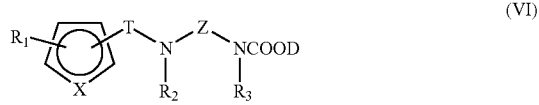

Preferably the compound (V) is $(R_2)_2SO_4$, in particular $Et_2SO_4$, and the reaction is carried out in an in inert organic solvent, which does not change in the reaction conditions, and at a temperature between 80° C. and 170° C., in particular at substantially 111° C.

The solvents that can be used include: ethers, such as diethyl ether or tetrahydrofuran; halogenated hydrocarbons, such as dichloromethane, trichloromethane, tetrachloromethane, 1,2-dichloroethane, trichloroethane, tetrachloroethane, 1,2-dichloroethylene or trichloroethylene; hydrocarbons, such as benzene, xylene, toluene, hexane, cyclohexane or petroleum ether, nitromethane, dimethylformamide, acetone or acetonitrile. It is also possible to use mixtures of the solvents mentioned. Toluene is the solvent particularly preferred for this reaction.

At this point, the carbamic function is hydrolysed in the compound (VI) in order to obtain a compound having a general formula (VII):

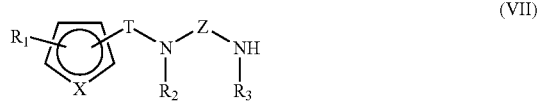

Hydrolysis preferably takes place in an acid environment and the solvent used is acetic acid. According to a particularly preferred embodiment, HBr is used for hydrolysis.

At this point on a p-benzoquinone having a general formula (VIII):

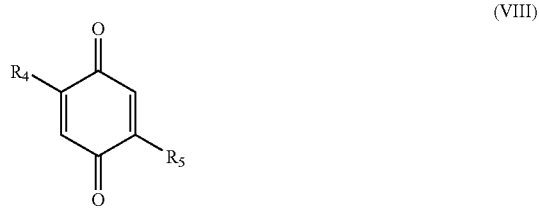

a substitution is made with the compound (VII) in order to obtain the 2,5-bis-diamine-[1,4]benzoquinonic derivative having a general formula (I).

Surprisingly, the 2,5-bis-diamine-[1,4]benzoquinonic derivative having a general formula (I) has shown a relatively high activity for the treatment of Alzheimer's disease (AD) in mammals.

Moreover, surprisingly, the 2,5-bis-diamine-[1,4]benzoquinonic derivative having a general formula (I) has presented a relatively very high activity of inhibition of the enzyme acetylcholinesterase (AChE).

In particular, the 2,5-bis-diamine-[1,4]benzoquinonic derivative having a general formula (I) has presented an activity of AChE inhibition relatively much higher than the activity of inhibition that the same 2,5-bis-diamine-[1,4]benzoquinonic derivative (I) presented with relation to the enzyme butyrylcholine esterase (BuChE).

In this regard, it is important to point out that the capacity of the 2,5-bis-diamine-[1,4]benzoquinonic derivative (I) to bind preferentially with AChe rather than with BuChE, avoids the 2,5-bis-diamine-[1,4]benzoquinonic derivative (I) being distracted from its primary objective (that is AChE). In the past it has been supposed that BuChE acts as an enzymatic system protecting AChE against false substrata.

Moreover, the 2,5-bis-diamine-[1,4]benzoquinonic derivative having a general formula (I) surprisingly presents an inhibiting activity with regard to the aggregation of Aβ induced by AChE.

It is important to stress that the quinonic functionality presents a protective antioxidant activity with respect to the oxidative stress due to the accumulation of Aβ. The inhibiting activity with regard to the aggregation of Aβ and the antioxidant activity, surprisingly, combine synergically to substantially improve the conditions of patients affected by pathologies characterised by deposits of Aβ.

In particular, it is important to stress that the relatively very high AChE inhibiting activity, the relatively low BuChE inhibiting activity, the inhibiting activity with regard to the aggregation of Aβ and the antioxidant activity, surprisingly, combine synergically to substantially improve the conditions of patients affected by Aβ.

The 2,5-bis-diamine-[1,4]benzoquinonic derivatives (I) or their pharmaceutically acceptable salts, can be administered as pure compounds, however they are preferably presented in the form of a pharmaceutical formula. Non limiting examples of suitable pharmaceutical formulae are listed below.

The 2,5-bis-diamine-[1,4]benzoquinonic derivatives (I) can be formulated for oral, parenteral or rectal administration or in forms suited for administration by inhalation or insufflation (both by mouth and by nose). Formulae for oral or parenteral administration are preferred.

For oral administration, the pharmaceutical preparations can be, for example, in the form of tablets or capsules prepared using known methods with excepients acceptable from a pharmaceutical point of view as binding agents (for example pre-gelatised corn starch, polyvinylpyrrolidone or methylcellulose); fillers (for example lactose, microcrystalline cellulose or calcium hydrogen phosphate); additives (for example magnesium stearate, talc, silica); disintegrants (for example potato starch); and/or lubricating agents (for example sodium lauryl sulphate). The tablets can be coated with known methods. Liquid preparations for oral administration may have the form, for example, of syrupy solutions or suspensions, or they can be in the form of a dry product which can be dissolved in water or in another liquid before use. These preparations can be prepared in known ways with pharmaceutically acceptable additives such as suspending agents (for example sorbitol, cellulose derivatives, edible hydrogenated fats); emulsifying agents (for example lecithin or acacia); non aqueous liquids (for example almond oil, oily esters, ethyl alcohol or fractionated vegetable oils); and/or preservatives (for example methyl or propylphydroxybenzoates, sorbic acid or ascorbic acid). The preparations can also contain, in appropriate cases, buffering salts, colouring, aromatic and/or sweetening agents. Preparations for oral administration can be formulated in a known way, so as to give a controlled release of the active compound.

The 2,5-bis-diamine-[1,4]benzoquinonic derivatives (I) can be formulated, in a known way, for parenteral administration by injection or continuous administration. Formulae for injection may be in the form of single doses, for example in ampoules or multidose containers containing preservatives. The composition may be in the form of a suspension, in aqueous or oily liquids, and it may contain formulation elements such as dispersing and stabilising agents. Alternatively, the active compound may be in powder form to be dissolved immediately before use in a suitable liquid, for example sterilised water.

The 2,5-bis-diamine-[1,4]benzoquinonic derivatives (I) can be formulated for rectal administration as suppositories or enteroclysis, for example containing excipients for suppositories of a known type such as cocoa butter or other fats.

The 2,5-bis-diamine-[1,4]benzoquinonic derivatives (I) can also be formulated, in a known way, as compositions with prolonged release. These compositions with prolonged release can be administered by means of an implant (for example subcutaneous, or intramuscular) or by means of an intramuscular injection. So, for example, the 2,5-bis-diamine-[1,4]benzoquinonic derivatives (I) can be formulated with suitable polymeric or hydrophobic materials (for example an emulsion or an oil) or resins with ionic exchange, or relatively poorly soluble derivatives, such as relatively poorly soluble salts.

For intranasal administration, the 2,5-bis-diamine-[1,4] benzoquinonic derivatives (I) can be formulated for administration by means of a (known) device, for example in powder form with a suitable carriers.

The dosages of the 2,5-bis-diamine-[1,4]benzoquinonic derivatives (I) will depend on the age and conditions of the patient, so the precise dosage must be decided from time to time by the doctor. The dosage will also depend on the means of administration and on the particular compound selected. Usable doses may be for example between 0.1 mg/Kg and 400 mg/Kg with respect to body weight per day.

The 2,5-bis-diamine-[1,4]benzoquinonic derivatives (I), can be administered in combination with one or more suitable therapeutic agents and formulated in every known usable way.

Further characteristics of the present invention will appear more clearly from the following description which refers to embodiments taken purely as examples and without limitation.

EXAMPLE 1

This example describes the synthesis of the acid [3-(2-methoxy-benzylamino)-propyl]-carbamic benzyl ester (IX) having the formula:

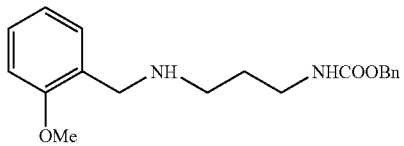

To a solution of (3-amino-propyl)-carbamic benzyl ester acid (1.04 g, 5 mmol) in 50 ml of ethanol containing molecular sieves (4 Å), 2-methoxybenzaldehyde was added (0.75 g, 5.5 mmol). The mixture was left in agitation at environment temperature (e.t.) for 20 min, then $NaBH_4$ was added when cold (0.2 g, 5 mmol). It was left to react for 6 h, it was acidified cautiously with HCl 2N, the sieves were filtered and the solvents were evaporated; the residue was taken again with $H_2O$ and extracted with diethyl ether (3×10 ml). The aqueous solution was then basified with NaOH 40% and extracted with $CHCl_3$ (4×20 ml). The anhydrified and evaporated organic extracts gave 1.5 g of the compound IX as pure transparent oil on TLC (eluant: $CHCl_3/EtOH/NH_4OH$ 9.0: 1.0:0.1). Yield 90%; $^1H$ NMR (free base; $CDCl_3$) δ: 1.61-1.79 (m, 2H+1H exchangeable with $D_2O$), 2.70 (t, 2H), 3.32 (q, 2H), 3.78 (s, 2H), 3.84 (s, 3H), 5.11 (s, 2H), 5.73 (s enlarged, 1H exchangeable with $D_2O$), 6.84-6.95 (m, 2H), 7.19-7.40 (m, 7H).

EXAMPLE 2

This example describes the synthesis of the acid {3-[ethyl-(2-methoxy-benzyl)-amino]-propyl}-carbamic benzyl ester (X) having the formula:

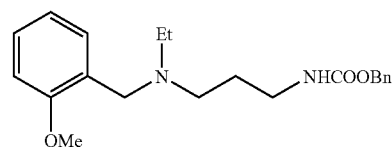

To a solution of [3-(2-methoxy-benzylamino)-propyl]-carbamic benzyl ester acid (1.4 g; 4.3 mmol) in 70 ml of toluene diethyl sulphate was added (1.24 ml; 9.5 mmol) and heated by reflux for 24 h. The reaction mixture was cooled at e.t. and beaten with conc. NaOH (50 ml). The organic phase was separated, which after anhydrification and evaporation gave a crude material which was purified by flash chromatography. Eluting with $CH_2Cl_2$/ether of petroleum/MeOH/$NH_4OH$ 4.6: 5.0:0.4:0.04 obtained 1.4 g of the compound X as pure transparent oil on TLC (eluant: $CHCl_3/MeOH/NH_4OH$ 9.5:0.5: 0.05). Yield 91%; $^1H$ NMR (free base; $CDCl_3$) δ: 1.08 (t, 3H), 1.61-1.79 (m, 2H), 2.53-2.75 (m, 4H), 3.32 (q, 2H), 3.78 (s, 2H), 3.84 (s, 3H), 5.11 (s, 2H), 5.73 (s enlarged, 1H exchangeable with $D_2O$), 6.84-6.95 (m, 2H), 7.19-7.40 (m, 7H).

EXAMPLE 3

This example describes the synthesis of $N^1$-ethyl-$N^1$-(2-methoxy-benzyl)-propan-1,3-diamine (XI) having the formula:

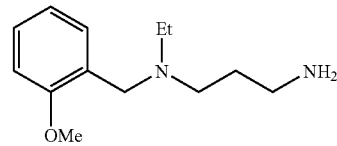

To a solution of {3-[ethyl-(2-methoxy-benzyl)-amino]-propyl}-carbamic benzyl ester acid (1.4 g; 3.9 mmol) in 15 ml of glacial $CH_3COOH$, 3.5 ml of a 33% solution of HBr in $CH_3COOH$ was added cautiously. It was left in agitation for 2 h, then the hydrobromate was precipitated with 100 ml of diethyl ether. The white solid formed was solubilised in $H_2O$, basified with NaOH 2N and extracted with $CHCl_3$ (5×20 ml). The anhydrified organic phase was evaporated in a vacuum to give 0.87 g of the compound XI as pure transparent oil on TLC (eluant $CHCl_3/MeOH/NH_4OH$ 9.0:1.0:0.1); quantity yield; $^1H$ NMR (free base; $CDCl_3$) δ: 1.07 (t, 3H), 1.50 (s enlarged, 2H exchangeable with $D_2O$), 1.57-1.71 (m, 2H), 2.55 (q, 4H), 2.73 (t, 2H), 3.60 (s, 2H), 3.84 (s, 3H), 6.83-6.99 (m, 2H), 7.19-7.44 (m, 2H).

EXAMPLE 4

This example describes the synthesis of 2,5-Bis-{3-[ethyl-(2-methoxy-benzyl)-amino]-propylamino}-[1,4]benzoquinone (XII) having the formula:

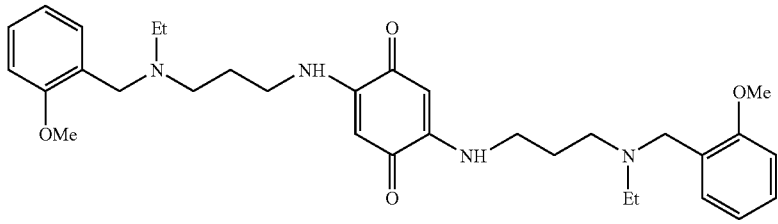

To a solution of p-benzoquinone (0.1 g; 0.92 mmol) in 70 ml of MeOH was added when cold $N^1$-ethyl-$N^1$-(2-methoxy-benzyl)-propan-1,3-diamine (0.45 g; 2.0 mmol). The reaction mixture was agitated at e.t. and out of the light for 6 h, the was evaporated in a vacuum to give a crude material which was purified by flash chromatography. Eluting with $CH_2Cl_2$/MeOH/$NH_4OH$ 9.75:0.25:0.025 obtained 0.23 g of the compound XII as a pure red solid on TLC (eluant: $CHCl_3$/MeOH/$NH_4OH$ 9.5:0.5:0.05). Yield 45%; $^1H$ NMR (free base; $CDCl_3$) δ: 1.11 (t, 6H), 1.72-1.85 (m, 4H), 2.56 (q, 8H), 3.18 (q, 4H), 3.62 (s, 4H), 3.82 (s, 6H), 5.26 (s, 2H), 6.83-6.95 (m, 4H), 7.19-7.43 (m, 4H+2H exchangeable with $D_2O$); EI-MS: m/z=548 ($M^+$).

EXAMPLE 5

This example describes the synthesis of the acid [6-(2-methoxy-benzylamine-hexyl]-carbamic benzyl ester (XIII):

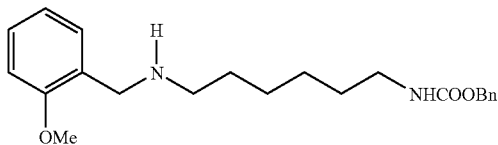

The compound XIII was obtained as a transparent oil from the acid (6-amino-hexyl)-carbamic benzyl ester (2.50 g, 10 mmol) following the same procedure described in example 1; yield 81%; $^1H$ NMR (free base; $CDCl_3$) δ: 1.22-1.38 (m, 4H), 1.41-1.57 (m. 4H), 1.65 (s enlarged, 1H exchangeable with $D_2O$), 2.58 (t, 2H), 3.18 (q, 2H), 3.77 (s, 2H), 3.84 (s, 3H), 4.76 (s enlarged, 1H exchangeable with $D_2O$), 5.09 (s, 2H), 6.82-6.93 (m, 2H), 7.20-7.40 (m, 7H).

EXAMPLE 6

This example describes the synthesis of the acid {6-[ethyl-(2-methoxy-benzyl)-amino]-hexyl}-carbamic benzyl ester (XIV):

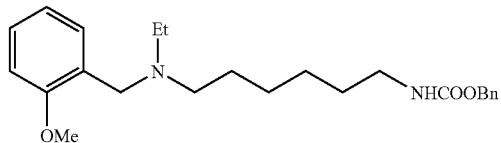

The compound XIV was obtained as a transparent oil from the acid [6-(2-methoxy-benzylamino)-hexyl]-carbamic benzyl ester (2.91 g, 7.85 mmol) following the same procedure described in example 2. Yield 76%; $^1H$ NMR (free base; $CDCl_3$) δ: 1.05 (t, 3H), 1.21-1.32 (m, 4H), 1.40-1.57 (m. 4H), 2.41-2.59 (m, 4H), 3.16 (q, 2H), 3.60 (s, 2H), 3.80 (s, 3H), 4.73 (s enlarged, 1H exchangeable with $D_2O$), 5.08 (s, 2H), 6.82-6.94 (m, 2H), 7.18-7.42 (m, 7H).

EXAMPLE 7

This example describes the synthesis of $N^1$-ethyl-$N^1$-(2-methoxy-benzyl)-hexan-1,6-diamine (XV):

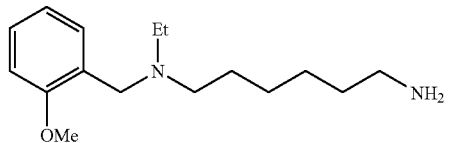

The compound XV was obtained as a transparent oil from the acid {6-[ethyl-(2-methoxy-benzyl)-amino]-hexyl}-carbamic benzyl ester (2.31 g; 6.01 mmol) following the same procedure described in example 3. Yield 98%; $^1H$ NMR (free base; $CDCl_3$) δ: 1.04 (t, 3H), 1.12-1.48 (m, 8H+2H exchangeable with $D_2O$), 2.41-2.53 (m, 4H), 2.65 (t, 2H), 3.57 (s, 2H), 3.81 (s, 3H), 6.82-6.94 (m, 2H), 7.16-7.42 (m, 2H).

EXAMPLE 8

This example describes the synthesis of 2,5-Bis-{6-[ethyl-(2-methoxy-benzyl)-amino]-hexylamino}-[1,4]benzoquinone (XVI):

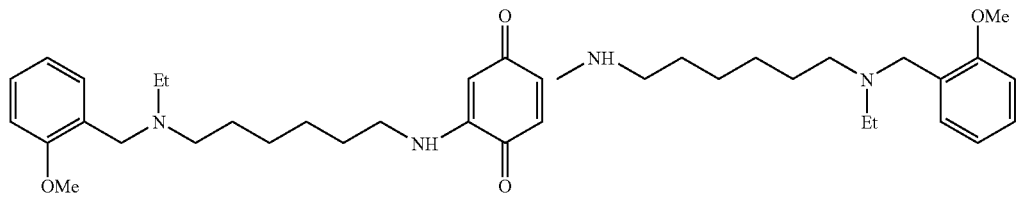

The compound XVI was obtained as a red solid from $N^1$-ethyl-$N^1$-(2-methoxy-benzyl)-hexan-1,6-diamine (1.05 g; 4 mmol) and p-benzoquinone (0.2 g; 1.84 mmol) following the same procedure described in example 4. Yield 17%; $^1$H NMR (free base; CDCl$_3$) δ: 1.04 (t, 6H), 1.14-1.38 (m, 8H), 1.43-1.53 (m, 4H), 1.57-1.65 (m, 4H), 2.41-2.56 (m, 8H), 3.10 (q, 4H), 3.57 (s, 4H), 3.81 (s, 6H), 5.28 (s, 2H), 6.59 (t enlarged, 2H exchangeable with D$_2$O), 6.83-6.95 (m, 4H), 7.21 (t, 2H), 7.39 (d, 2H). EI-MS: m/z=632 (M$^+$).

EXAMPLE 9

This example describes the synthesis of 2,5-Bis-[6-(benzyl-ethyl-amino)-hexylamino]-[1,4]benzoquinone (XVII):

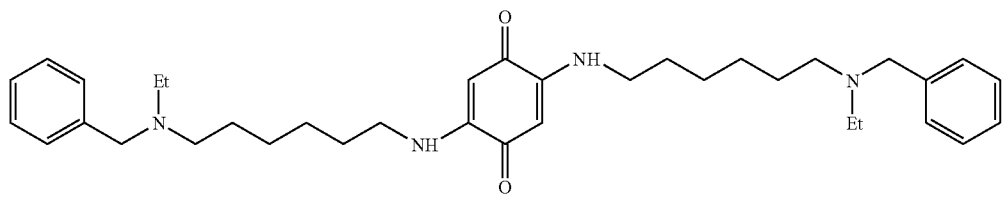

The compound XVII was obtained as a red solid from $N^1$-ethyl-$N^1$-benzyl-hexan-1,6-diamine (0.47 g; 2 mmol) and p-benzoquinone (0.1 g; 0.92 mmol) following the same procedure described in example 8. Yield 20%; $^1$H NMR (free base; CDCl$_3$) δ: 1.05 (t, 6H), 1.14-1.39 (m, 8H), 1.43-1.53 (m, 4H), 1.58-1.65 (m, 4H), 2.41-2.56 (m, 8H), 3.10 (q, 4H), 3.71 (s, 4H), 5.28 (s, 2H), 6.44 (t enlarged, 2H exchangeable with D$_2$O), 7.10-7.24 (m, 10H). EI-MS: m/z=572 (M$^+$). $N^1$-ethyl-$N^1$-benzyl-hexan-1,6-diamine was obtained with procedures similar to those described in examples 1-4 using corresponding starting compounds.

EXAMPLE 10

This example describes the synthesis of 2,5-Bis-{6-[ethyl-(2-chloro-benzyl)-amino]-hexylamino}-[1,4]benzoquinone (XVIII):

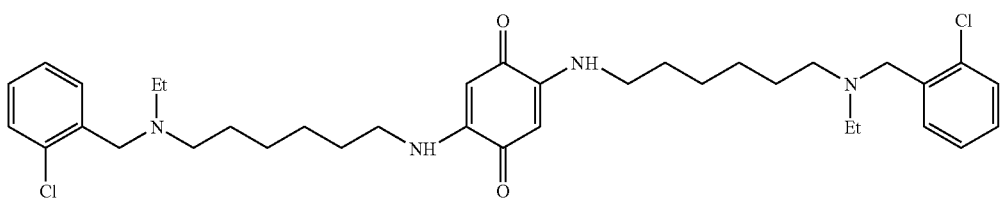

The compound XVIII was obtained as a red solid from $N^1$-ethyl-$N^1$-(2-chloro-benzyl)-hexan-1,6-diamine (0.54 g; 2 mmol) and p-benzoquinone (0.1 g; 0.92 mmol) following the same procedure described in example 8. Yield 15%; $^1$H NMR (free base; CDCl$_3$) δ: 1.04 (t, 6H), 1.10-1.35 (m, 8H), 1.43-1.53 (m, 4H), 1.57-1.65 (m, 4H), 2.41-2.56 (m, 8H), 3.08 (q, 4H), 3.46 (s, 4H), 5.28 (s, 2H), 6.59 (t enlarged, 2H exchangeable with D$_2$O), 7.05-7.23 (m, 6H), 7.45 (d, 2H). EI-MS: m/z=641 (M$^+$). $N^1$-ethyl-$N^1$-(2-chloro-benzyl)-hexan-1,6-diamine was obtained with procedures similar to those described in examples 1-4 using corresponding starting compounds.

EXAMPLE 11

This example describes the synthesis of 2,5-Di-tert-butyl-3,6-bis-{3-[ethyl-(2-methoxy-benzyl)-amino]-propylamino}-[1,4]benzoquinone (XIX):

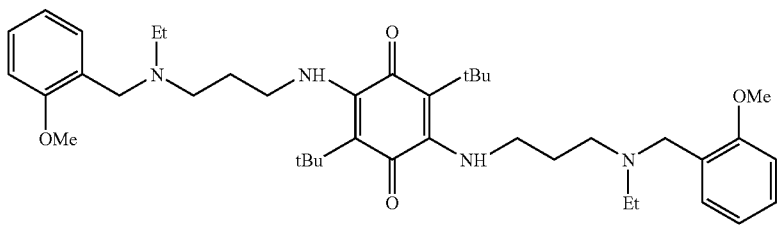

The compound XIX was obtained as a fuchsia coloured solid from the compound having the formula XI (90 mg; 0.40 mmol) and 2,5-di-tert-butyl-[1,4]benzoquinone (40 mg; 0.18 mmol), following the same procedure described in example 8. Yield 10%; $^1$H NMR (free base; CDCl$_3$) δ: 1.09 (t, 6H), 1.15 (s, 9H), 1.27 (s, 9H), 1.70-1.83 (m, 4H), 2.52-2.64 (m, 8H), 3.15 (s, 3H), 3.54-3.71 (m, 4H), 3.83 (s, 3H), 6.81-6.96 (m, 4H), 7.18-7.44 (m, 4H). EI-MS: m/z=660 (M$^+$).

EXAMPLE 12

This example describes the synthesis of the acid [6-benzylamino-hexyl]-carbamic benzyl ester (XX) having the formula:

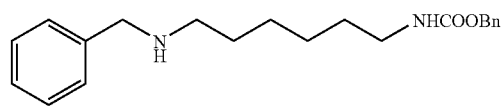

The compound XX was obtained as a transparent oil from the acid (6-amino-hexyl)-carbamic benzyl ester (4.00 g, 16 mmol) following the same procedure described in example 1. Quantity yield; $^1$H NMR (free base; CDCl$_3$) δ: 1.22-1.57 (m, 6H+1H exchangeable with D$_2$O), 1.78-1.97 (m, 2H), 2.75 (t, 2H), 3.18 (q, 2H), 4.05 (s, 2H), 5.01 (t enlarged, 1H exchangeable with D$_2$O), 5.15 (s, 2H), 7.30-7.45 (m, 8H), 7.57-7.65 (m, 2H).

EXAMPLE 13

This example describes the synthesis of the acid [6-(ethyl-benzyl-amino)-hexyl]-carbamic benzyl ester (XXI):

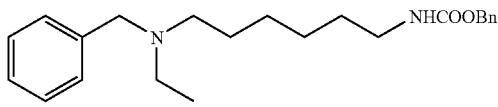

The compound XXI was obtained as a transparent oil from the acid [6-benzylamino-hexyl]-carbamic benzyl ester (5.00 g, 14 mmol) following the same procedure described in example 2. Yield 30%; $^1$H NMR (free base; CDCl$_3$) δ: 1.10 (t, 3H), 1.22-1.40 (m, 4H), 2.40-2.62 (m, 4H), 3.16 (q, 2H), 3.58 (s, 2H), 5.05 (s enlarged, 1H exchangeable with D$_2$O), 5.18 (s, 2H), 7.22-7.40 (m, 10H).

EXAMPLE 14

This example describes the synthesis of N$^1$-ethyl-N$^1$-benzyl-hexan-1,6-diamine (XXII):

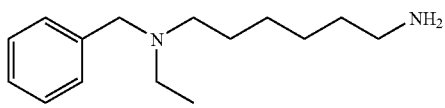

The compound XXII was obtained as a transparent oil from the acid {6-[ethyl-benzyl-amino]-hexyl}-carbamic benzyl ester (0.9 g; 2.45 mmol) following the same procedure described in example 3. Quantity yield; $^1$H NMR (free base; CDCl$_3$) δ: 1.03 (t, 3H), 1.15 (s enlarged, 2H exchangeable with D$_2$O), 1.21-1.58 (m, 8H), 2.37-2.58 (m, 4H), 2.65 (t, 2H), 3.56 (s, 2H), 7.20-7.38 (m, 5H).

EXAMPLE 15

This example describes the synthesis of the acid [6-(2-chloro-benzylamino-hexyl]-carbamic benzyl ester (XXIII):

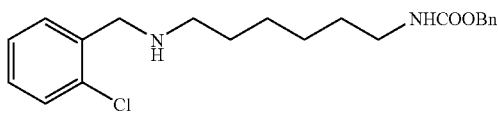

The compound XXIII was obtained as a transparent oil from the acid (6-amino-hexyl)-carbamic benzyl ester (4.00 g, 16 mmol) following the same procedure described in example 1. Yield 65%; $^1$H NMR (free base; CDCl$_3$) δ: 1.23-1.60 (m, 8H), 2.41 (br, s 1H exchangeable with D$_2$O), 2.61 (t, 2H), 3.17 (q, 2H), 3.89 (s, 2H), 4.84 (s enlarged, 1H exchangeable with D$_2$O), 5.12 (s, 2H), 7.18-7.40 (m, 9H).

EXAMPLE 16

This example describes the synthesis of the acid {6-[ethyl-(2-chloro-benzyl)-amino]-hexyl}-carbamic benzyl ester (XXIV):

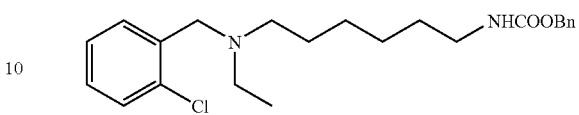

The compound XXIV was obtained as a transparent oil from the acid [6-(2-chloro-benzylamino)-hexyl]-carbamic benzyl ester (2.00 g, 5.35 mmol) following the same procedure described in example 2. Yield 40%; $^1$H NMR (free base; CDCl$_3$) δ: 1.08 (t, 3H), 1.21-1.58 (m, 8H), 2.40-2.62 (m, 4H), 3.15 (q, 2H), 3.63 (s, 2H), 4.82 (s enlarged, 1H exchangeable with D$_2$O), 5.12 (s, 2H), 7.10-7.41 (m, 8H), 7.57 (d, 1H).

EXAMPLE 17

This example describes the synthesis of N$^1$-ethyl-N$^1$-(2-chloro-benzyl)-hexan-1,6-diamine (XXV):

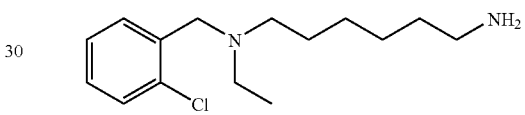

The compound XXV was obtained as a yellow oil from the acid {6-[ethyl-(2-chloro-benzyl)-amino]-hexyl}-carbamic benzyl ester (0.80 g; 1.99 mmol) following the same procedure described in example 3. Yield 98%; $^1$H NMR (free base; CDCl$_3$) δ: 1.05 (t, 3H), 1.12-1.54 (m, 8H+2H exchangeable with D$_2$O), 2.38-2.66 (m, 6H), 3.61 (s, 2H), 7.05-7.37 (m, 3H), 7.53 (d, 1H).

EXAMPLE 18

This example describes the synthesis of the acid [6-(2-nitro-benzylamino)-hexyl]-carbamic benzyl ester (XXVI):

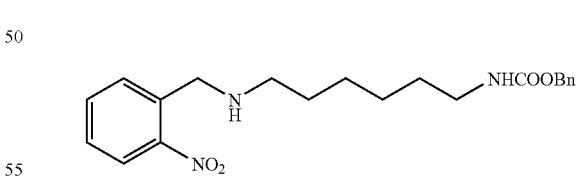

The compound XXVI was obtained as a transparent oil from the acid (6-amino-hexyl)-carbamic benzyl ester (5.00 g, 20 mmol) following the same procedure described in example 1. Yield 95%; $^1$H NMR (free base; CDCl$_3$) δ: 1.27-1.38 (m, 4H), 1.42-1.60 (m, 4H+1H exchangeable with D$_2$O), 2.62 (t, 2H), 3.18 (q, 2H), 4.02 (s, 2H), 4.89 (s enlarged, 1H exchangeable with D$_2$O), 5.12 (s, 2H), 7.24-7.42 (m, 6H), 7.58-7.66 (m, 2H), 7.95 (d, 1H).

EXAMPLE 19

This example describes the synthesis of the acid {6-[ethyl-(2-nitro-benzyl)-amino]-hexyl}-carbamic benzyl ester (XXVII):

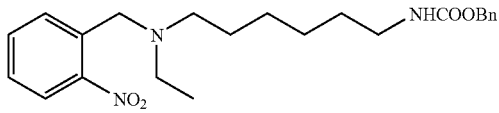

The compound XXVII was obtained as a greenish oil from the acid [6-(2-nitro-benzylamino)-hexyl]-carbamic benzyl ester (3.00 g, 7.79 mmol) following the same procedure described in example 2. Yield 40%; $^1$H NMR (free base; CDCl$_3$) δ: 1.02 (t, 3H), 1.20-1.57 (m, 8H), 2.37-2.56 (m, 4H), 3.18 (q, 2H), 3.83 (s, 2H), 4.76 (s enlarged, 1H exchangeable with D$_2$O), 5.12 (s, 2H), 7.29-7.41 (m, 6H), 7.50-7.61 (m, 1H), 7.66-7.72 (m, 1H), 7.79-7.83 (m, 1H).

EXAMPLE 20

This example describes the synthesis of N$^1$-ethyl-N$^1$-(2-nitro-benzyl)-hexan-1,6-diamine (XXVIII):

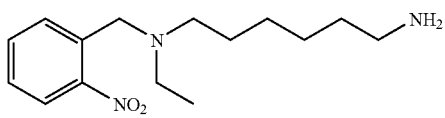

The compound XXVIII was obtained as a yellow oil from the acid {6-[ethyl-(2-nitro-benzyl)-amino]-hexyl}-carbamic benzyl ester (0.80 g; 2.00 mmol) following the same procedure described in example 3. Yield 98%; $^1$H NMR (free base; CDCl$_3$) δ: 1.02 (t, 3H), 1.20-1.57 (m, 8H), 2.05 (s enlarged, 2H exchangeable with D$_2$O), 2.37-2.56 (m, 4H), 2.73 (t, 2H), 3.83 (s, 2H), 7.32-7.41 (m, 1H), 7.50-7.61 (m, 1H), 7.70-7.76 (m, 1H), 7.79-7.83 (m, 1H).

EXAMPLE 21

This example describes the synthesis of 2,5-bis-{6-[ethyl-(2-nitro-benzyl)-amino]-hexylamino}-[1,4]benzoquinone (XXIX):

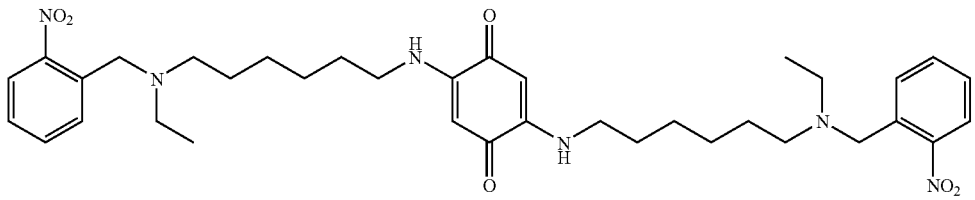

The compound XXIX was obtained as a waxy red solid from N$^1$-ethyl-N$^1$-(2-nitro-benzyl)-hexan-1,6-diamine (0.65 g; 2.33 mmol) and p-benzoquinone (0.12 g; 1.1 mmol) following the same procedure described in example 4. Yield 15%; $^1$H NMR (free base; CDCl$_3$) δ: 0.98 (t, 6H), 1.19-1.50 (m, 12H), 1.52-1.72 (m, 4H), 2.35-2.57 (m, 8H), 3.13 (q, 4H), 3.83 (s, 4H), 5.30 (s, 2H), 6.58-6.66 (t enlarged, 2H exchangeable with D$_2$O), 7.32-7.41 (m, 2H), 7.48-7.58 (m, 2H), 7.62-7.70 (m, 2H), 7.78-7.82 (m, 2H). MS (ESI$^+$) m/z=663 (M+H)$^+$.

EXAMPLE 22

This example describes the synthesis of the acid [6-(3-methoxy-benzylamino-hexyl]-carbamic benzyl ester (XXX):

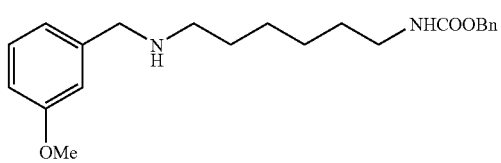

The compound XXX was obtained as a transparent oil from the acid (6-amino-hexyl)-carbamic benzyl ester (4.00 g, 16 mmol) following the same procedure described in example 1. Yield 76%; $^1$H NMR (free base; CDCl$_3$) δ: 1.22-1.38 (m, 4H), 1.41-1.62 (m, 4H), 2.58 (s enlarged, 1H exchangeable with D$_2$O), 2.62 (t, 2H), 3.18 (q, 2H), 3.78 (s, 2H), 3.81 (s, 3H), 4.83 (s enlarged, 1H exchangeable with D$_2$O), 5.08 (s, 2H), 6.79-6.95 (m, 3H), 7.20-7.41 (m, 6H).

EXAMPLE 23

This example describes the synthesis of the acid {6-[ethyl-(3-methoxy-benzyl)-amino]-hexyl}-carbamic benzyl ester (XXXI):

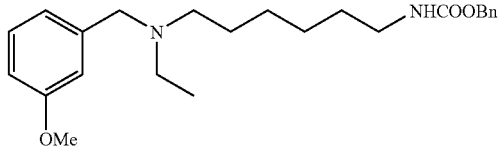

The compound XXXI was obtained as a transparent oil from the acid [6-(3-methoxy-benzylamino)-hexyl]-carbamic benzyl ester (2.91 g, 7.85 mmol) following the same procedure described in example 2. Yield 50%; $^1$H NMR (free base; CDCl$_3$) δ: 1.05 (t, 3H), 1.21-1.38 (m, 4H), 1.40-1.57 (m, 4H), 2.43 (t, 2H), 2.73 (t, 2H), 3.18 (q, 2H), 3.56 (s, 2H), 3.80 (s, 3H), 4.83 (s enlarged, 1H exchangeable with D$_2$O), 5.09 (s, 2H), 6.79-6.82 (m, 1H), 6.85-6.88 (m, 2H), 7.22 (t, 1H), 7.29-7.42 (m, 5H).

EXAMPLE 24

This example describes the synthesis of $N^1$-ethyl-$N^1$-(3-methoxy-benzyl)-hexan-1,6-diamine (XXXII):

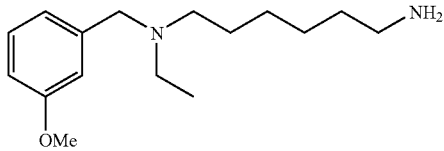

The compound XXXII was obtained as a transparent oil from the acid {6-[ethyl-(3-methoxy-benzyl)-amino]-hexyl}-carbamic benzyl ester (2.31 g; 6.01 mmol) following the same procedure described in example 3. Yield 90%; $^1$H NMR (free base; CDCl$_3$) δ: 1.04 (t, 3H), 1.22-1.65 (m, 8H+2H exchangeable with D$_2$O), 2.38-2.58 (m, 4H), 2.65 (t, 2H), 3.58 (s, 2H), 3.82 (s, 3H), 6.72-6.92 (m, 3H), 7.16-7.29 (m, 1H).

EXAMPLE 25

This example describes the synthesis of 2,5-bis-{6-[ethyl-(3-methoxy-benzyl)-amino]-hexylamino}-[1,4]benzoquinone (XXXIII):

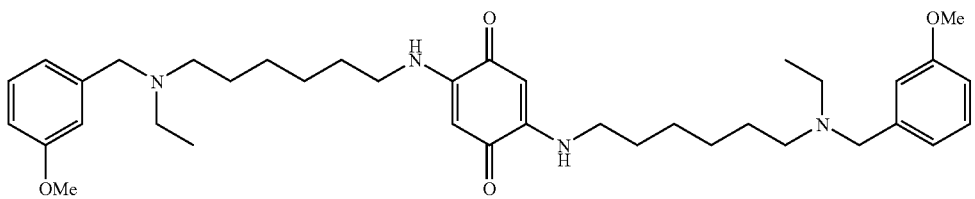

The compound XXXIII was obtained as a waxy red solid from $N^1$-ethyl-$N^1$-(3-methoxy-benzyl)-hexan-1,6-diamine (1.0 g; 4.24 mmol) and p-benzoquinone (0.2 g; 1.84 mmol) following the same procedure described in example 4. Yield 15%; $^1$H NMR (free base; CDCl$_3$) δ: 1.04 (t, 6H), 1.24-1.57 (m, 12H), 1.60-1.75 (m, 4H), 2.39-2.60 (m, 8H), 3.09 (q, 4H), 3.57 (s, 4H), 3.81 (s, 6H), 5.32 (s, 2H), 6.63 (t enlarged, 2H exchangeable with D$_2$O), 6.76-6.95 (m, 6H), 7.18-7.28 (t, 2H). MS (ESI$^+$) m/z=633 (M+H)$^+$.

EXAMPLE 26

This example describes the synthesis of the acid [6-(4-methoxy-benzylamino-hexyl]-carbamic benzyl ester (XXXIV):

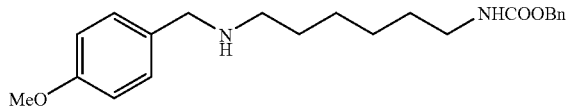

The compound XXXIV was obtained as a yellow oil from the acid (6-amino-hexyl)-carbamic benzyl ester (2.50 g, 10 mmol) following the same procedure described in example 1; yield 90%; $^1$H NMR (free base; CDCl$_3$) δ: 1.25-1.38 (m, 4H), 1.41-1.57 (m, 4H+1H exchangeable with D$_2$O), 2.62 (t, 2H), 3.19 (q, 2H), 3.75 (s, 2H), 3.82 (s, 3H), 4.76 (s enlarged, 1H exchangeable with D$_2$O), 5.12 (s, 2H), 6.82-6.93 (m, 2H), 7.20-7.43 (m, 7H).

EXAMPLE 27

This example describes the synthesis of the acid {6-[ethyl-(4-methoxy-benzyl)-amino]-hexyl}-carbamic benzyl ester (XXXV):

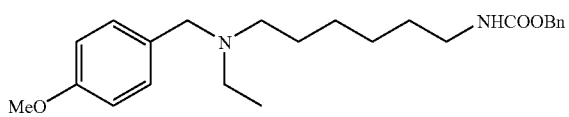

The compound XXXV was obtained as a transparent oil from the acid [6-(2-methoxy-benzylamino)-hexyl]-carbamic benzyl ester (2.91 g, 7.85 mmol) following the same procedure described in example 2. Yield 40%; $^1$H NMR (free base; CDCl$_3$) δ: 1.07 (t, 3H), 1.23-1.38 (m, 4H), 1.42-1.57 (m, 4H), 2.42 (t, 2H), 2.56 (q, 2H), 3.21 (q, 2H), 3.52 (s, 2H), 3.82 (s, 3H), 4.83 (s enlarged, 1H exchangeable with D$_2$O), 5.12 (s, 2H), 6.84 (d, 2H), 7.25 (d, 2H), 7.32-7.42 (m, 5H).

EXAMPLE 28

This example describes the synthesis of $N^1$-ethyl-$N^1$-(4-methoxy-benzyl)-hexan-1,6-diamine (XXXVI):

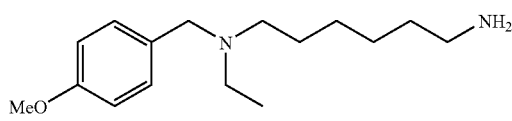

The compound XXXVI was obtained as a transparent oil from the acid {6-[ethyl-(4-methoxy-benzyl)-amino]-hexyl}-carbamic benzyl ester (2.31 g; 6.01 mmol) following the same procedure described in example 3. Quantity yield; $^1$H NMR (free base; CDCl$_3$) δ: 1.06 (t, 3H), 1.22-1.56 (m, 8H+2H exchangeable with D$_2$O), 2.38-2.57 (m, 4H), 2.66 (t, 2H), 3.55 (s, 2H), 3.81 (s, 3H), 6.82-6.94 (m, 2H), 7.20-7.31 (m, 2H).

EXAMPLE 29

This example describes the synthesis of 2,5-bis-{6-[ethyl-(4-methoxy-benzyl)-amino]-hexylamino}-[1,4]benzoquinone (XXXVII):

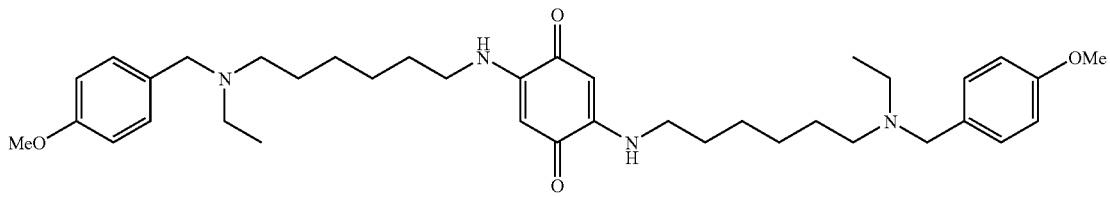

The compound XXXVII was obtained as a waxy red solid from N¹-ethyl-N¹-(4-methoxy-benzyl)-hexan-1,6-diamine (1.05 g; 4 mmol) and p-benzoquinone (0.2 g; 1.84 mmol) following the same procedure described in example 4. Yield 12%; $^1$H NMR (free base; CDCl$_3$) δ: 1.04 (t, 6H), 1.22-1.56 (m, 12H), 1.58-1.72 (m, 4H), 2.38-2.56 (m, 8H), 3.12 (q, 4H), 3.47 (s, 4H), 3.79 (s, 6H), 5.32 (s, 2H), 6.59 (t enlarged, 2H exchangeable with D$_2$O), 6.82-6.93 (m, 4H), 7.21-7.30 (m, 4H). MS (ESI$^+$) m/z=633 (M+H)$^+$.

EXAMPLE 30

This example describes the synthesis of the acid {6-[(furan-2-ilmethyl)amino]-hexyl}-carbamic benzyl ester (XXXVIII):

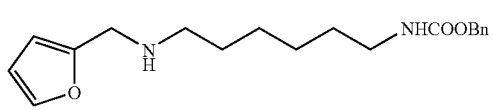

The compound XXXVIII was obtained as a brown solid from (6-amino-hexyl)-carbamic benzyl ester (4.00 g, 16 mmol) following the same procedure described in example 1. Yield 72%; $^1$H NMR (free base; CDCl$_3$) δ: 1.22-1.50 (m, 8H), 1.73-1.98 (m, 2H+1H exchangeable with D$_2$O), 2.69-2.94 (m, 2H), 3.18 (q, 2H), 4.28 (s, 2H), 4.99-5.18 (m, 2H+1H exchangeable with D$_2$O), 6.39-6.42 (m, 1H), 6.72-6.79 (m, 1H), 7.28-7.40 (m, 5H), 7.46-7.50 (m, 1H). P.f.=132-135° C.

EXAMPLE 31

This example describes the synthesis of the acid [6-(ethyl-furan-2-ilmethyl-amino)-hexyl]-carbamic benzyl ester (XXXIX):

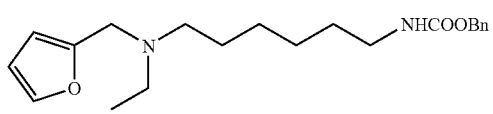

The compound XXXIX was obtained as a yellow oil from the acid {6-[(furan-2-ilmethyl)amino]-hexyl}-carbamic benzyl ester (2.70 g, 8.18 mmol) following the same procedure described in example 2. Yield 35%; $^1$H NMR (free base; CDCl$_3$) δ: 1.15-1.60 (m, 9H), 1.82-1.99 (m, 2H), 2.79-2.88 (m, 2H), 2.99 (q, 2H), 3.21 (q, 2H), 4.22 (s, 2H), 4.96 (s enlarged, 1H exchangeable with D$_2$O), 5.15 (s, 2H), 6.43-6.49 (m, 1H), 6.62-6.68 (m, 1H), 7.32-7.41 (m, 5H), 7.53-7.56 (m, 1H).

EXAMPLE 32

This example describes the synthesis of N¹-ethyl-N¹-furan-2-ilmethyl-hexan-1,6-diamine (XL):

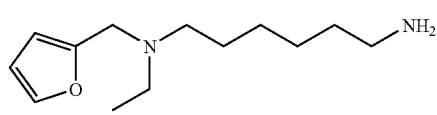

The compound XL was obtained as a transparent oil from the acid [6-(ethyl-furan-2-ilmethyl-amino)-hexyl]-carbamic benzyl ester (1.05 g; 2.92 mmol) following the same procedure described in example 3. Yield 85%; $^1$H NMR (free base; CDCl$_3$) δ: 1.08 (t, 3H), 1.22-1.58 (m, 8H+2H exchangeable with D$_2$O), 2.38-2.61 (m, 4H), 2.67 (t, 2H), 3.62 (s, 2H), 6.18-6.20 (m, 1H), 6.32-6.38 (m, 1H), 7.38-7.42 (m, 1H).

EXAMPLE 33

This example describes the synthesis of 2,5-bis-[6-(ethyl-furan-2-ilmethyl-amino)-hexylamino]-[1,4]benzoquinone (XLI):

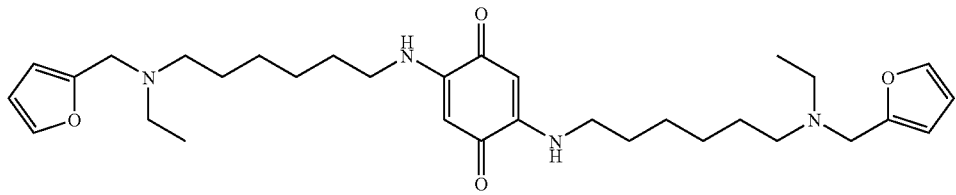

The compound XLI was obtained as a waxy red solid from $N^1$-ethyl-$N^1$-furan-2-ilmethyl-hexan-1,6-diamine (0.55 g; 2.45 mmol) and p-benzoquinone (0.14 g; 1.23 mmol) following the same procedure described in example 4. Yield 16%; $^1$H NMR (free base; CDCl$_3$) δ: 1.09 (t, 6H), 1.22-1.58 (m, 12H), 1.60-1.73 (m, 4H), 2.43 (t, 4H), 2.57 (q, 4H), 3.18 (q, 4H), 3.63 (s, 4H), 5.32 (s, 2H), 6.18-6.22 (m, 2H), 6.32-6.39 (m, 2H), 6.62 (t enlarged, 2H exchangeable with D$_2$O), 7.38-7.41 (m, 2H). MS (ESI$^+$) m/z=553 (M+H)$^+$.

EXAMPLE 34

This example describes the synthesis of the acid [2-(2-methoxy-benzylamino-ethyl]-carbamic benzyl ester (XLII):

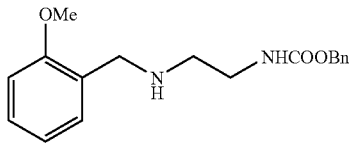

The compound XLII was obtained as a yellow oil from the acid (2-amino-ethyl)-carbamic benzyl ester (5.00 g, 25.8 mmol) following the same procedure described in example 1. Yield 80%; $^1$H NMR (free base; CDCl$_3$) δ: 1.63 (s enlarged, 1H exchangeable with D$_2$O), 2.75 (t, 2H), 3.33 (q, 2H), 3.78 (s, 2H), 3.83 (s, 3H), 5.18 (s, 2H), 5.38 (s enlarged, 1H exchangeable with D$_2$O), 6.82-6.93 (m, 2H), 7.20-7.41 (m, 7H).

EXAMPLE 35

This example describes the synthesis of the acid {2-[ethyl-(2-methoxy-benzyl)-amino]-ethyl}-carbamic benzyl ester (XLIII):

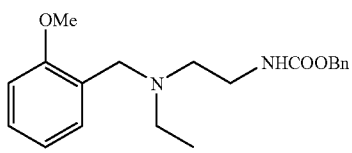

The compound XLIII was obtained as a transparent oil from the acid [2-(2-methoxy-benzylamino)-ethyl]-carbamic benzyl ester (2.00 g, 19.7 mmol) following the same procedure described in example 2. Yield 45%; $^1$H NMR (free base; CDCl$_3$) δ: 1.05 (t, 3H), 2.58 (q, 2H), 2.62 (t, 2H), 3.38 (q, 2H), 3.62 (s, 2H), 3.82 (s, 3H), 5.20 (s, 2H), 5.78 (s enlarged, 1H exchangeable with D$_2$O), 6.85-6.99 (m, 2H), 7.23-7.44 (m, 7H).

EXAMPLE 36

This example describes the synthesis of $N^1$-ethyl-$N^1$-(2-methoxy-benzyl)-ethan-1,2-diamine (XLIV):

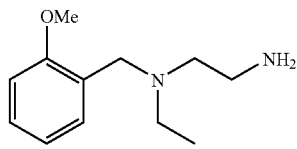

The compound XLIV was obtained as a transparent oil from the acid {2-[ethyl-(2-methoxy-benzyl)-amino]-ethyl}-carbamic benzyl ester (1.50 g; 4.35 mmol) following the same procedure described in example 3. Yield 98%; $^1$H NMR (free base; CDCl$_3$) δ: 1.04 (t, 3H), 2.00 (s enlarged, 2H exchangeable with D$_2$O), 2.65 (q, 2H), 2.98 (t, 2H), 3.21 (t, 2H), 3.78 (s, 2H), 3.85 (s, 3H), 6.85-7.01 (m, 2H), 7.20-7.42 (m, 2H).

EXAMPLE 37

This example describes the synthesis of 2,5-bis-{2-[ethyl-(2-methoxy-benzyl)-amino]-ethylamino}-[1,4]benzoquinone (XLV):

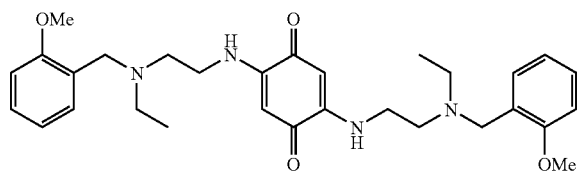

The compound XLV was obtained as a dark red solid from $N^1$-ethyl-$N^1$-(2-methoxy-benzyl)-ethan-1,2-diamine (1.40 g; 6.27 mmol) and p-benzoquinone (0.34 g; 3.12 mmol) following the same procedure described in example 4. Yield 10%; $^1$H NMR (free base; CD$_3$OD) δ: 1.15 (t, 6H), 2.64 (q, 4H), 2.79 (t, 4H), 3.71 (s, 4H), 3.82 (s, 6H), 5.28 (s, 2H), 6.88-6.99 (m, 4H), 7.21-7.38 (m, 4H). MS (ESI$^+$) m/z=521 (M+H)$^+$. Pf: 127-130° C.

EXAMPLE 38

This example describes the synthesis of the acid [7-(2-methoxy-benzylamino-heptyl)]-carbamic benzyl ester (XLVI):

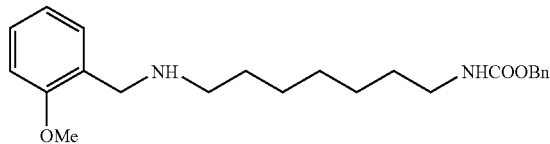

The compound XLVI was obtained as a yellow oil from the acid (7-amino-heptyl)-carbamic benzyl ester (2.50 g, 9.4 mmol) following the same procedure described in example 1. Yield 90%; $^1$H NMR (free base; CDCl$_3$) δ: 1.22-1.38 (m, 6H), 1.38-1.64 (m, 4H+1H exchangeable with D$_2$O), 2.62 (t, 2H), 3.13 (q, 2H), 3.81 (s, 3H), 3.84 (s, 2H), 5.09 (s, 2H), 5.22 (s enlarged, 1H exchangeable with D$_2$O), 6.80-6.93 (m, 2H), 7.19-7.40 (m, 7H).

EXAMPLE 39

This example describes the synthesis of the acid {7-[ethyl-(2-methoxy-benzyl)-amino]-heptyl}-carbamic benzyl ester (XLVII):

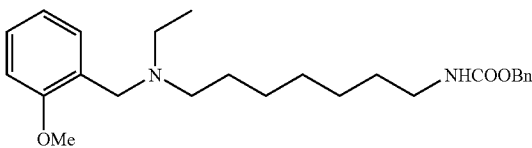

The compound XLVII was obtained as a transparent oil from the acid [7-(2-methoxy-benzylamino)-heptyl]-carbamic benzyl ester (3.30 g, 8.0 mmol) following the same procedure described in example 2. Yield 35%; $^1$H NMR (free base; CDCl$_3$) δ: 1.12 (t, 3H), 1.25-1.38 (m, 6H), 1.43-1.61 (m, 4H), 2.45-2.61 (m, 4H), 3.20 (q, 2H), 3.65 (s, 2H), 3.83 (s, 3H), 5.02 (s enlarged, 1H exchangeable with D$_2$O), 5.19 (s, 2H), 6.84-7.02 (m, 2H), 7.21-7.51 (m, 7H).

EXAMPLE 40

This example describes the synthesis of N$^1$-ethyl-N$^1$-(2-methoxy-benzyl)-heptan-1,7-diamine (XLVIII):

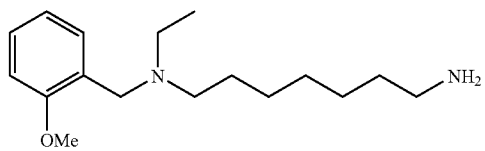

The compound XLVIII was obtained as a yellow oil from the acid {7-[ethyl-(2-methoxy-benzyl)-amino]-heptyl}-carbamic benzyl ester (1.10 g; 2.50 mmol) following the same procedure described in example 3. Quantity yield; $^1$H NMR (free base; CDCl$_3$) δ: 0.98 (t, 3H), 1.12-1.53 (m, 10H+2H exchangeable with D$_2$O), 2.35-2.52 (m, 4H), 2.55-2.63 (m, 2H), 3.55 (s, 2H), 3.72 (s, 3H), 6.72-6.80 (m, 1H), 6.83 (t, 1H), 7.14 (t, 1H), 7.38 (d, 1H).

EXAMPLE 41

This example describes the synthesis of 2,5-bis-{7-[ethyl-(2-methoxy-benzyl)-amino]-heptylamino}-[1,4]benzoquinone (IL):

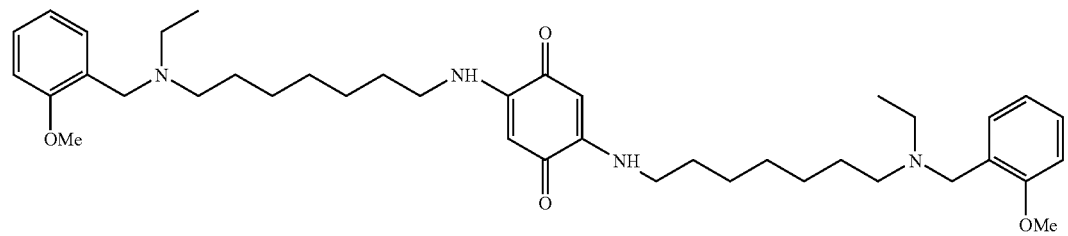

The compound IL was obtained as a red oil from N$^1$-ethyl-N$^1$-(2-methoxy-benzyl)-heptan-1,7-diamine (0.90 g; 3.23 mmol) and p-benzoquinone (0.17 g; 1.57 mmol) following the same procedure described in example 4. Yield 12%; $^1$H NMR (free base; CDCl$_3$) δ: 1.08 (t, 6H), 1.28-1.42 (m, 12H), 1.45-1.60 (m, 4H), 1.62-1.75 (m, 4H), 2.48 (t, 4H), 2.58 (q, 4H), 3.18 (q, 4H), 3.62 (s, 4H), 3.83 (s, 6H), 5.35 (s, 2H), 6.62 (t enlarged, 2H exchangeable with D$_2$O), 6.85-6.90 (m, 2H), 6.97 (t, 2H), 7.22 (t, 2H), 7.43 (d, 2H). MS (ESI$^+$) m/z=661 (M+H)$^+$.

EXAMPLE 42

This example describes the synthesis of N-(2-methoxy-benzyl)-hexan-1,6-diamine (L):

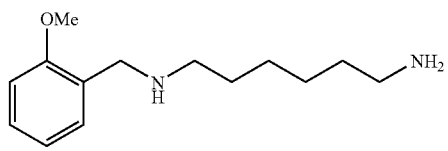

The compound L was obtained as a yellow oil from the acid [6-(2-methoxy-benzylamino-hexyl)]-carbamic benzyl ester (2.0 g; 5.40 mmol) following the same procedure described in example 3. Yield 65%; $^1$H NMR (free base; CDCl$_3$) δ: 1.12-

1.42 (m, 8H+3H exchangeable with D$_2$O), 2.38-2.56 (m, 4H), 3.60 (s, 2H), 3.62 (s, 3H), 6.63-6.79 (m, 2H), 7.01-7.15 (m, 2H).

EXAMPLE 43

This example describes the synthesis of 2,5-bis-[6-(2-methoxy-benzylamino)-hexylamino]-[1,4]-benzoquinone (LI):

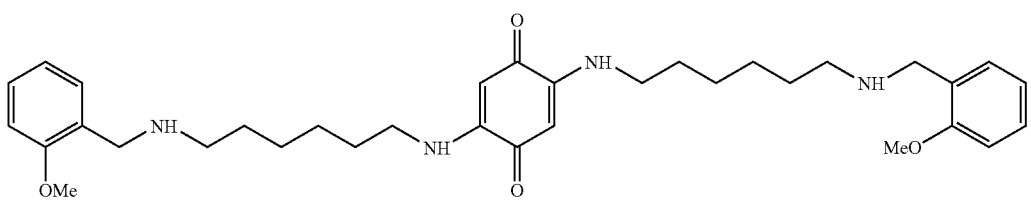

The compound LI was obtained as a red solid from N-(2-methoxy-benzyl)-hexan-1,6-diamine (0.70 g; 2.96 mmol) and p-benzoquinone (0.15 g; 1.38 mmol) following the same procedure described in example 4. Yield 18%; $^1$H NMR (free base; CDCl$_3$) δ: 1.28-1.42 (m, 8H), 1.52-1.76 (m, 8H), 2.63 (t, 4H), 3.16 (q, 4H), 3.78-3.85 (m, 10+2H exchangeable with D$_2$O), 5.32 (s, 2H), 6.62 (t enlarged, 2H exchangeable with D$_2$O), 6.85-6.96 (m, 4H), 7.22-7.35 (m, 4H). MS (ESI$^+$) m/z=577 (M+H)$^+$. Pf: 205° C.

EXAMPLE 44

This example describes the synthesis of the acid {6-[(2-methoxy-benzyl)-methyl-amino]-hexyl}-carbamic benzyl ester (LII):

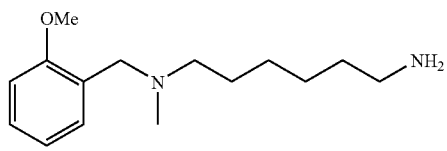

To a suspension of the acid [6-(2-methoxy-benzylamino-hexyl]-carbamic benzyl ester (5.0 g; 13.5 mmol) in 8 ml of H$_2$O are added HCOOH (1.6 ml; 40.5 mmol) and HCHO (3.1 ml; 40.5 mmol). It was left in agitation by reflux for 6 hours and at e.t. for one night, then the aqueous solution was basified with NaOH 40% and extracted with CHCl$_3$ (3×100 ml). The collected and anhydrified organic extracts were evaporated in a vacuum and the residue obtained was purified by flash chromatography. Eluting with CHCl$_3$/ether of petroleum/MeOH/NH$_4$OH (8:2:0.7:0.05) obtained 1.6 g of the compound LII as a yellow oil. Yield 75%; $^1$H NMR (free base, CDCl$_3$) δ: 1.23-1.39 (m, 4H), 1.40-1.63 (m, 4H), 2.23 (s, 3H), 2.44 (t, 2H), 3.17 (q, 2H), 3.58 (s, 2H), 3.82 (s, 3H), 5.12 (s, 2H), 5.22 (s enlarged, 1H exchangeable with D$_2$O), 6.82-7.00 (m, 2); 7.20-7.38 (m, 7).

EXAMPLE 45

This example describes the synthesis of N$^1$-(2-methoxy-benzyl)-N$^1$-methyl-1,6 hexandiamine (LIII):

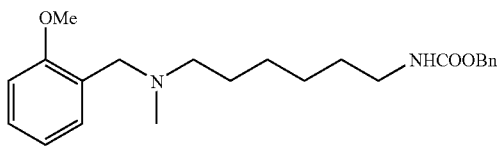

The compound LIII was obtained as a yellow oil from the acid {6-[(2-methoxy-benzyl)-methyl-amino]-hexyl}-carbamic benzyl ester (1.60 g; 4.20 mmol) following the same procedure described in example 3. Quantity yield; $^1$H NMR (free base; CDCl$_3$) δ: 1.18-1.56 (m, 8H+2H exchangeable with D$_2$O), 2.18 (s, 3H), 2.38 (t, 2H), 2.62 (t, 2H), 3.45 (s, 2H), 3.78 (s, 3H), 6.78-6.92 (m, 2H), 7.19 (t, 1H), 7.28-7.31 (m, 1H).

EXAMPLE 46

This example describes the synthesis of 2,5-bis-{6-[(2-methoxy-benzyl)-methylamino]-hexylamino}-[1,4]-benzoquinone (LIV).

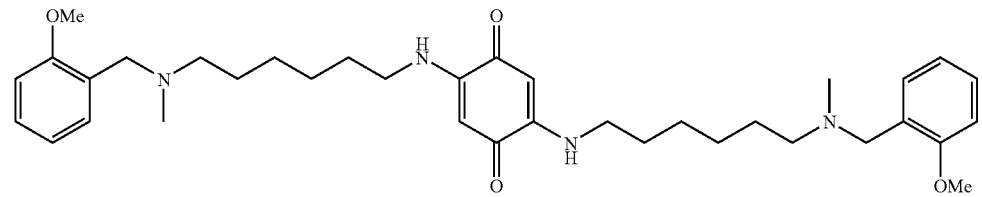

The compound LIV was obtained as a waxy red solid from N$^1$-(2-methoxy-benzyl)-N$^1$-methyl-1,6 hexandiamine (0.90 g; 3.60 mmol) and p-benzoquinone (0.18 g; 1.66 mmol) following the same procedure described in example 4. Yield 10%; $^1$H NMR (free base; CDCl$_3$) δ: 1.31-1.48 (m, 16H), 2.22 (s, 6H), 2.41 (t, 4H), 3.15 (q, 4H), 3.52 (s, 4H), 3.83 (s, 6H), 5.32 (s, 2H), 6.62 (t enlarged, 2H exchangeable with D$_2$O), 6.83-6.99 (m, 4H), 7.19-7.38 (m, 4H). MS (ESI$^+$) m/z=605 (M+H)$^+$.

EXAMPLE 47

This example describes the synthesis of 2,5-bis-{6-[ethyl-(2-methoxy-benzyl)-amino]-hexylamino}-3,6-dimethyl-[1,4]-benzoquinone (LV).

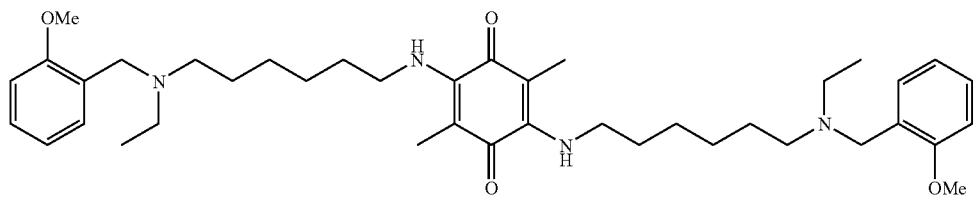

The compound LV was obtained as a red oil from N$^1$-(2-methoxy-benzyl)-N$^1$-ethyl-1,6 hexandiamine (0.82 g; 3.10 mmol) and 2,5-dimethyl-benzoquinone (0.20 g; 1.85 mmol) following the same procedure described in example 4. Yield 10%; $^1$H NMR (free base; CDCl$_3$) δ: 1.12 (t, 6H), 1.22-1.43 (m, 8H), 1.45-1.63 (m, 8), 2.11 (s, 6H), 2.48-2.62 (m, 8H), 3.53 (q, 4H), 3.63 (s, 4H), 3.83 (s, 6H), 6.72 (t enlarged, 2H exchangeable with D$_2$O), 6.83-7.01 (m, 4H), 7.23 (t, 2H), 7.42 (m, 2H). MS (ESI$^+$) m/z=661 (M+H)$^+$.

EXAMPLE 48

This example describes the determination of the inhibiting capacity and of the selectivity of the compounds XVI and XII and the comparison of these properties with some drugs present on the market.

The inhibiting power (IC$_{50}$) was determined using Ellman's spectrophotometric method (Ellman, G. L.; Courtney, K. D.; Andres, V.; Featherstone, R. M. A New and Rapid Colorimetric Determination of Acetylcholinesterase Activity. Biochem. Pharmacol. 1961, Vol. 7, p. 88-95).

The value of IC$_{50}$ was determined using constant concentrations of substratum and enzyme and varying the concentration of an inhibitor with successive increases. In this way the activity of the enzyme was determined on the basis of revelations of the formation of an anionic coloured molecular species (2-nitro 4-thiobenzoate) ($λ_{max}$=412 nm), which is obtained following the reaction between thiocholine—a product of the enzymatic hydrolysis of acetylthiocholine (substratum of AChE) or butyrylthiocholine (substratum of BuChE)—and 5,5' dithio-bis-nitrobenzoic acid (Ellman's reactive). The variation of absorbance at 412 nm (that is the variation of the absorbance of 2-nitro 4-thiobenzoate per minute (ΔA/min) (enzymatic speed) depends on the substratum concentration, and on the enzymatic activity of AChE (from human erythrocytes, amphiphilic form, EC 3.1.1.7) and BuChE (from human serum, EC 3.1.1.8), according to the kinetic of Michaelis Menten.

To calculate the IC$_{50}$, constant concentrations of saturating substratum were used, that is which were able to produce maximum enzymatic speed (V$_{max}$) and fixed enzyme rates. Five growing concentrations of the compounds under study were then tested, able to induce inhibitions of between 20% and 1'80% of the V$_{max}$. Lines of inhibition were next obtained, plotting on a graph the percentage of inhibition of the V$_{max}$ as a function of the decimal logarithm of the nanomolar concentration of the inhibitor. The parameters of linear regression were assessed for each line and the IC$_{50}$ (the concentration able to inactivate the maximum enzymatic activity by 50%), which was obtained by interpolation on the respective line.

TABLE I

| Inhibitor | IC$_{50(AChE)}$ (nM) | IC$_{50\,(BuChE)}$ (nM) | Selectivity IC$_{50(BuChE)}$/IC$_{50\,(AChE)}$ |
|---|---|---|---|
| XII | 3.19 ± 0.15$^a$ | 4490 ± 340$^a$ | 1407 |
| XVI | 2.39 ± 0.14$^a$ | 1440 ± 100$^a$ | 602 |
| Tacrine | 250 ± 10 | 50 ± 2 | 0.2 |
| Donepezil | 5.7$^b$ | ~7000$^b$ | ~1200 |

$^a$Mean of two independent measurements, repeated in triplicate;
$^b$Sugimoto, H.; Yamanishi, Y.; Iimura, Y.; Kawakami, Y.; Donepezil hydrochloride (E2020) and other Acetylcholinesterase inhibitors. Current Medicinal Chemistry 2000, vol. 7, p. 303-339.

Table I shows the IC$_{50}$ obtained using the method described above and relating to the compounds XVI, XII, to Tacrine and to Donepezil. The IC$_{50}$ for the AChE are indicated as IC$_{50}$ $_{(AChE)}$, the IC$_{50}$ for BuChE are indicated as IC$_{50(BuChE)}$. The selectivity is defined as the ratio between IC$_{50(AChE)}$ and IC$_{50(BuChE)}$ and indicates the inhibitor's ability to bind preferably with AChE rather than with BuChE.

Compounds XVI and XII showed a relatively very good IC$_{50(AChE)}$ (Table I), two times smaller than the IC$_{50(AChE)}$ of Tacrine (Cognex®) and substantially lower than that of Donepezil (Aricept®).

The selectivity was relatively very good, higher than that of Tacrine and comparable to that of Donepezil.

EXAMPLE 49

This example describes the determination of an inhibiting constant (K$_i$) of the compound XVI.

The assessment of the kinetic of an inhibitor can supply important information on the nature of the bond between enzyme and inhibitor, the site or sites of the bond and the quantitative efficacy of the bond, expressed by K$_i$. K$_i$ in fact describes the state of equilibrium between a free enzyme (in the particular case AChE, from human erythrocytes EC 3.1.1.7), an inhibitor (in the particular case the compound XVI) and the enzyme-inhibitor complex, representing the disassociation constant of the enzyme-inhibitor complex.

Figure 2:
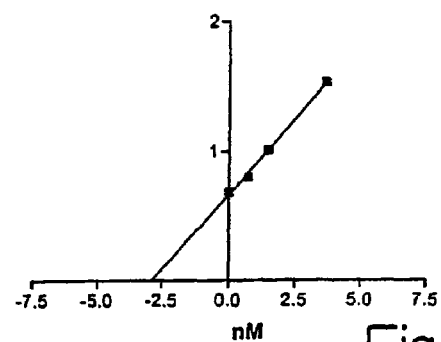
FIG. 2 illustrates an experimental graph depicting the gradient function of the lines of the graph in FIG. 1 with relation to the concentrations of a 2,5-bis-diamine-[1,4]benzoquinonic derivative having a general formula (I)

The determination of the K$_i$ of the complex AChE-compound XVI was realised using the method of Lineweaver- Burk (Dixon, M., Webb, E. C., *Enzymes*, Second Edition, Chapter VIII, p. 315, Longmans, Green and Co. Ltd, 1964, London, UK). For each concentration of the compound XVI the enzymatic activity was assessed with the variation of the concentration of the substratum acetylthiocholine (111-550 µM). The data obtained on enzymatic activity were plotted on a graph (FIG. 1) showing for each concentration of the compound XVI, the reciprocal of the speed as a function of the inverse of the concentration of the substratum. The values of the gradients of the lines obtained for each concentration of inhibitor were then plotted on a graph (FIG. 2) as a function of the corresponding concentration of inhibitor. The intercept on the axis of the X-coordinates of the line obtained, not passing through zero, gave a value of $K_i$ equal to 2.6 nM for the compound XVI.

From the analysis of the graph of Lineweaver-Burk (FIG. 1) lines with growing gradients can be seen which show a change of both $V_{max}$ and $K_i$ in the presence of an inhibitor. This behaviour probably indicates a competitive inhibition of a mixed type, which springs from a significant interaction of the compound XVI both with the free enzyme and with the acetylated enzyme. From these results it seems that the compound XVI has a relatively strong interaction, not only with the active site, but also with another accessory site, potentially represented by the peripheral site of the enzyme. The compound XVI is therefore a relatively powerful, reversible, rapid, competitive inhibitor of a mixed type, which substantially follows the kinetic of Michaelis Menten.

EXAMPLE 50

The compounds in the following table were tested with the method of Ellman (see example 48) with recombining human AChE (HuAChE, EC 3.1.1.7) and on BuChE (from human serum, EC 3.1.1.8).

The table also shows the data concerning the inhibiting power of two reference compounds, Tacrine and Donepezil, tested in the same experimental conditions, and of the compounds XVI and XII.

| Compound | $IC_{50\ (HuAChE)}$ nM* | $IC_{50\ (BuChE)}$ nM* |
|---|---|---|
| XLV | 61.5 ± 1.3 | 16800 ± 1100 |
| XII | 2.25 ± 0.21 | 4490 ± 340 |
| XVI | 1.55 ± 0.11 | 1440 ± 100 |
| IL | 7.79 ± 0.37 | 1250 ± 250 |
| LIV | 77.8 ± 4.3 | 5110 ± 410 |
| LI | 123 ± 20 | 3230 ± 150 |
| LV | 9.50 ± 0.23 | 462 ± 2 |
| XVII | 73.3 ± 3.2 | 645 ± 33 |
| XXXVII | 51.1 ± 1.0 | 2420 ± 940 |
| XXXIII | 13.8 ± 1.7 | 2170 ± 70 |
| XXIX | 2310 ± 130 | 36500 ± 8800 |
| XVIII | 593 ± 51 | 45100 ± 1000 |
| XLI | 144 ± 3 | 3510 ± 180 |
| Tacrine | 424 ± 21 | 50 ± 2 |
| Donepezil | 23.1 ± 4.8 | 7420 ± 390 |

*Mean of two independent measurements, repeated in triplicate.

EXAMPLE 51

This example describes the determination of the amyloid anti-aggregating power of the compound XVI.

Since the induction of the formation of fibrils of Aβ by the AChE seems to occur by interaction between a peripheral site of the enzyme and the peptide (Inestrosa, N. C.; Alvarez, A.; Perez, C. A.; Moreno, R. D.; Vicente, M. et al. Acetylcholinesterase accelerates assembly of amyloid-beta-peptides into Alzheimer's fibrils: possible role of the peripheral site of the enzyme. *Neuron* 1996, Vol. 16, p. 881-891), and since the compound XVI seems to bind with this site, the ability of the compound XVI to inhibit the interaction between enzyme and Aβ and therefore to block the formation of fibrils induced by AChE was assessed. To do this a fluorimetric method was used which is able to highlight the ability of the AChE (recombining human, EC 3.1.1.7) to promote the formation of fibrils of the peptide Aβ (1-40).

Firstly Aβ (230 µM) was incubated with the enzyme (2.3 µM) in a molar ratio of 100:1, at environment temperature an aqueous phosphate buffer with pH=8.0, 0.215 M. To assess the formation of fibrils induced by AChE, the incubated solution was transferred into 2 ml of buffer with pH=8.5 composed of glycine-sodium hydroxide (50 mM), containing thioflavine T (1.5 µM). Thioflavine T interacts selectively with the fibrils of Aβ in beta conformation, developing a characteristic fluorescence. The intensity of fluorescence of this solution ($\lambda_{em}$=490 nm), after 300 s, was acquired, fixing the $\lambda_{exc}$=446 nm. A fluorescence scan of 300 s was then carried out to obtain a stable value of the fluorescent signal, from which was subtracted the contribution to the basic fluorescence of thioflavine T. To obtain the value of the intensity of fluorescence, relating only to the interaction of thioflavine T with the amyloid fibrils, the contributions of whites composed of Aβ and AChE incubated individually in the same conditions were subtracted.

Figure 3:
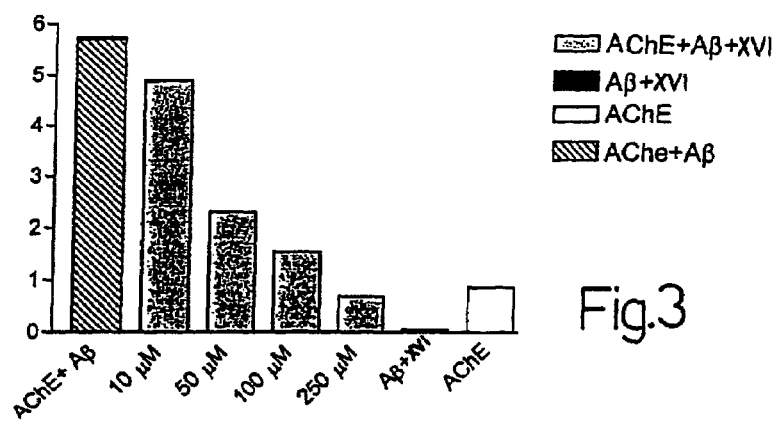
FIG. 3 illustrates the intensity of fluorescence (expressed in fluorescence units) of thioflavine complexed with fibrils of Aβ in the presence of variable concentrations of a 2,5-bis-diamine-[1,4]benzoquinonic derivative having a general formula (I)

Then, after having checked the conditions of aggregation of βA induced by AChE, the anti-aggregating power of the compound XVI was checked in the same conditions. The compound was incubated together with Aβ and AChE, in the same conditions described above. The concentration of the compound XVI was varied between 10 µM and 250 µM. In the presence of the compound XVI there was a lowering of the specific signal of intensity of fluorescence of thioflavine complexed with the fibrils of Aβ, indicating an amyloid anti-aggregating effect. The signal of fluorescence was directly proportional to the logarithm in base ten of the concentration of the compound XVI. The concentration of the compound XVI able to reduce the signal of fluorescence by 50% was equal to 28.3±0.3 µM (FIG. 3).

Among other AChE inhibiting compounds (that is Tacrine, Donepezil, physostigmine, propidium, decamethonium) tested in the conditions described, only propidium showed an inhibiting power ($IC_{50}$=12.6±0.3 µM) of the same magnitude as the inhibiting power of the compound XVI. On this point it is important to stress that propidium is described as a non competitive inhibitor of AChE, able to bind selectively with the peripheral site of the enzyme (Taylor, P.; Lappi, S. Interaction of fluorescence probes with acetylcholinesterase. The site and specificity of propidium binding. Biochemistry 1975, Vol. 14, p. 1989-1997). The anti-aggregating behaviour of the compound XVI therefore confirms that this molecule is able to establish binding interactions with the peripheral site of AChE, which has a high affinity for Aβ.

EXAMPLE 52

Following a method similar to the one described in the previous example, it was experimentally determined that the compound XII with a concentration of 100 µM exerts an inhibition of about 90% on the aggregation induced by AChE %.

EXAMPLE 53

This example describes the comparison between the $pIC_{50}$ of 2,5-bis-diamine-[1,4]benzoquinonic derivatives represented by the general formula (I) and known compounds having a general formula (LVI):

TABLE 2

(LVI)

$R_6\text{-}N(R_7)\text{-}(CH_2)_?\text{-}C(A)\text{=}N(R_8)\text{-}CH_2CH_2\text{-}E\text{-}CH_2CH_2\text{-}N(R_8)\text{=}C(A)\text{-}(CH_2)_?\text{-}N(R_7)R_6$

| No. | $R_6$ | $R_7$ | $R_8$ | A | E | $pIC_{50(AChE)}$ | $pIC_{50(BChE)}$ |
|---|---|---|---|---|---|---|---|
| 1 | 2-MeOC$_6$H$_5$CH$_2$ | H | H | H$_2$ | S—S | 5.14 ± 0.02 | 5.21 ± 0.03 |
| 2 | H | H | H | H$_2$ | S—S | 3.30 ± 0.03 | 3.19 ± 0.02 |
| 3 | 2-MeOC$_6$H$_5$CH$_2$ | H | H | H$_2$ | CH$_2$ | 5.14 ± 0.03 | 5.06 ± 0.02 |
| 4 | 2-MeOC$_6$H$_5$CH$_2$ | H | H | H$_2$ | (CH$_2$)$_2$ | 5.19 ± 0.01 | 5.86 ± 0.01 |
| 5 | 2-MeOC$_6$H$_5$CH$_2$ | H | H | H$_2$ | (CH$_2$)$_3$ | 5.35 ± 0.05 | 5.43 ± 0.02 |
| 6 | 2-MeOC$_6$H$_5$CH$_2$ | H | H | H$_2$ | (CH$_2$)$_4$ | 5.27 ± 0.03 | 6.01 ± 0.02 |
| 7 | 2-MeOC$_6$H$_5$CH$_2$ | H | H | O | (CH$_2$)$_4$ | 5.73 ± 0.03 | 4.94 ± 0.03 |
| 8 | 2-MeOC$_6$H$_5$CH$_2$ | H | Me | O | (CH$_2$)$_4$ | 6.51 ± 0.02 | 5.22 ± 0.04 |
| 9 | 2-MeOC$_6$H$_5$CH$_2$ | Me | Me | O | (CH$_2$)$_4$ | 6.77 ± 0.01 | 4.93 ± 0.04 |
| XII | | | | | | ≈8.49 | ≈5.35 |
| XVI | | | | | | ≈8.62 | ≈5.84 |

(The compounds having a general formula LVI are described in Melchiorre et al., Acetylcholinesterase noncovalent inhibitors based on a polyamine backbone for potential use against Alzheimer's disease, J. Med. Chem. 1998, vol. 41, 4186-4189).

It may be seen from table 2 that the 2,5-bis-diamine-[1,4] benzoquinonic derivatives represented by the general formula (I) present lower IC$_{50(AChE)}$ and higher selectivity than the known compounds having a general formula (LVI).

EXAMPLE 54

This example describes an assessment of the activity of the compound XVI in an animal model.

The tests in vivo were carried out using a recently realised animal model (Ruberti F, et al., J Neurosci 2000, Vol. 20, p. 2589-2601), which presents a phenotype strongly resembling Alzheimer's disease in man. In particular, the model consists of a transgenic mouse which expresses antibodies for the nerve growth factor (NGF), and consequently shows an extensive neuron loss in the cortex, formation of plaques of amyloid β and of intracellular neurofibrillar tangles, as well as dysfunctions in behaviour.

In particular, to produce the anti-NGF transgenic mice (AD11), the variable regions of the light and heavy chains of the anti-NGF monoclonal antibody αD11 were linked to the constant human regions k and γ1, to give the chimerical man/rat antibody αD11, and were then placed under the transcriptional control of the promoter of the precocious region of the human cytomegalovirus (CMV). Mice expressing functional anti-NGF antibodies (AD11 mice) were obtained by crossing mice that expressed the light chain (CMV-VK αD11) with mice that expressed the heavy chain (CMV-VH αD11).

The AD11 mice were treated with the compound XVI (7 mg/kg in saline solution) via intraperitoneal injection daily for 15 days from age 1.5 months to 2 months. Two control groups were considered: AD11 mice of the same litter treated with saline solution and non transgenic mice of the same stock and the same age.

The immunohistochemical tests were carried out as follows. The AD11 mice treated with the compound XVI, those treated with mice that expressed the and the non transgenic mice were anaesthetised with an overdose of chloral hydrate. The brain was removed and fixed for 24 h in a solution of 4% paraformaldehyde in phosphate buffer (PBS) and then cryo-protected in 30% sucrose. Coronal sections of the basal forebrain and of the entorhinal cortex were cut with a thickness of 40 µm and collected in 6-cell plates containing 1% paraformaldehyde in PBS. The following primary antibodies were used for the immunohistochemical analysis: anti-choline acetyltransferase (1:500, Chemicon Inc., Temecula, Calif.), anti-phosphorylated tau protein (clone AT8, Innogenetics N.V. Zwijnaarde, Belgium) and anti-protein precursor of amyloid (clone 2.F2.19B4 Chemicon Inc.). After incubation with the primary antibodies, the sections were washed before adding a biotinilated antibody against goat IgG (1:200, Vector Laboratories, Burlingame, Calif.) or against mouse IgG (Dako A/S, Glostrup, Denmark).

A stereological analysis was carried out to determine the number of cholinergic neurons positive to choline acetyltransferase (ChAT). The volume of the basal forebrain was calculated using the Cavalieri method described by Michel and Cruz-Olive (J Microsc 1988, Vol. 150, p. 117-146) and by Peterson et al. (J Comp Neurol 1999, Vol. 404, p. 1-20), while an estimate of the total number of neurons positive to ChAT was obtained using the optical fractionation method (West M J, Neurobiol Aging 1993, Vol. 14, p. 275-285; Peterson D A, et al., J Comp Neurol 1999, Vol. 404, p. 1-20).

Figure 5:
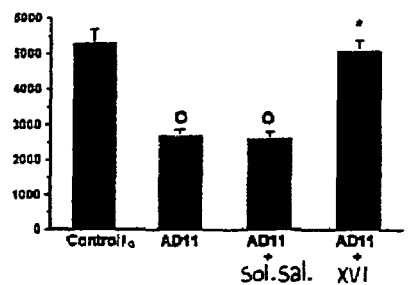
FIG. 5 illustrates the total number of cholinergic neurons in the basal forebrain.
Figure 6:
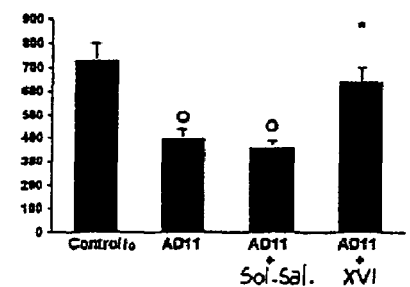
FIG. 6 illustrates the total number of cholinergic neurons in Meynert's basal nucleus.

To determine whether XVI can prevent the loss of ChAT positive neurons in the basal forebrain and in the basal nucleus of Meynert, the compound was administered daily to AD11 mice at a very early stage of neurodegeneration (from 1.5 months to 2 months; n=6). From the FIGS. 4A-4C it can be seen that the treatment was able to prevent the cholinergic deficit in the basal forebrain; the same result was quantified from the stereological calculations summed up in the graph in FIG. 5. Moreover, XVI was efficacious in preventing the loss of cholinergic neurons in the basal nucleus of Meynert, as indicated by the data shown in the graph in FIG. 6.

Figure 4:
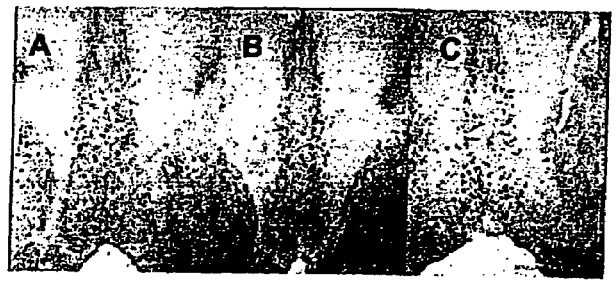
FIGS. 4A, 4B and 4C illustrate coronal sections of the basal forebrain of, respectively, non transgenic mice, transgenic mice (AD11) treated with a saline solution and transgenic mice (AD11) treated with a 2,5-bis-diamine-[1,4]benzoquinonic derivative having a general formula (I)
Figure 7:
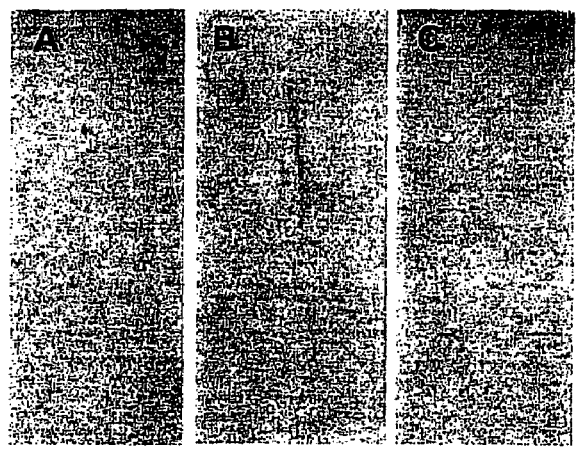
FIGS. 7A, 7B and 7C illustrate the depositions of APP in the cerebral vessels of, respectively, non transgenic mice, transgenic mice (AD11) treated with a saline solution, transgenic mice (AD11) treated with a 2,5-bis-diamine-[1,4]benzoquinonic derivative having a general formula (I)
Figure 8:
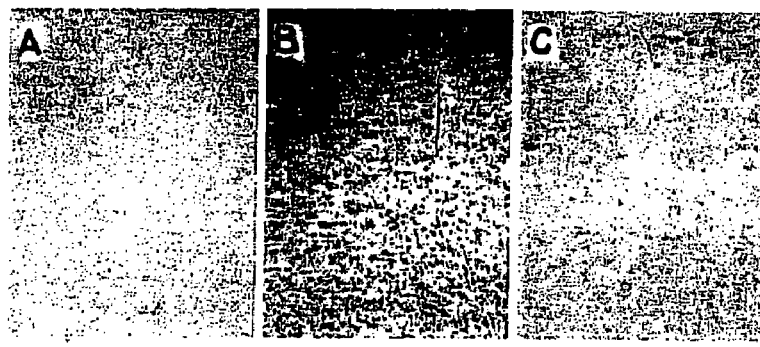
FIGS. 8A, 8B, 8C illustrate coronal sections of the entorhinal cortex of, respectively, non transgenic mice, transgenic mice (AD11) treated with a saline solution, transgenic mice (AD11) treated with a 2,5-bis-diamine-[1,4]benzoquinonic derivative having a general formula (I)

As regards other AD markers, the effect of XVI on the deposition of the amyloid β precursor protein (APP) and on tau protein hyperphosphorylation in AD11 mice of 2 months was examined. At age 2 months, APP deposition in the cerebral vessels is absent in the control mice (FIG. 7A), but important in the AD11 mice (FIG. 7B). APP deposition in the cerebral vessels is relatively prevented following the administration of XVI (FIG. 7C). From the comparison of FIGS. 7A, 7B and 7C, it may be deduced that the compound XVI was able to reduce markedly the cerebrovascular deposition of APP following administration for 15 days. To determine whether the compound XVI can prevent or recover tau hyperphosphorylation in the cortex, an immunohistochemical test was carried out on sections obtained from treated AD11 mice of 2 months and mice treated with the vehicle alone. While the control mice do not show hyperphosphorylated tau in the somatodendritic cellular compartment (FIG. 8A), the AD11 animals not treated or treated with the vehicle show an intense marking in the neuronal body (FIG. 4B). Tau hyperphosphorylation is partly prevented following the administration of XVI (FIG. 4C).

On conclusion of the experimental tests carried out in vivo in a transgenic model of AD, it may be said that the compounds of the invention present an activity profile compatible with the recovery of cholinergic functionality (increase of ChAT positive neurons) and the decrease of AD markers (decrease of the cerebrovascular deposition of APP and of tau hyperphosphorylation).

EXAMPLE 55

This example describes further assessments of the activity in vivo of the compound XVI in an animal model.

Doses and means of Administration

The compound XVI was dissolved in ethanol at a dose 50 times more concentrated than the one to be administered to the animal and then diluted in saline solution, for intraperitoneal injections, or in water, for oral administration.

To test its efficacy after oral administration, the compound XVI was administered in AD11 mice aged 15 months at a dose of 7 mg/kg/day.

To analyse the efficacy of the compound XVI in treating cognitive deficit in AD11 mice at age 6 and 12 months and in preventing the amnesia induced by scopolamine (Weiss B, Heller A. Methodological problems in evaluating the role of cholinergic mechanisms in behavior. Fed Proc 28, 135-146, 1969) a dose of 15 mg/kg/day was used, administered for 15 days.

At age 2 and 6 months, the capacity of the compound XVI in improving the Alzheimer phenotype in AD11 mice was compared to that of other inhibitors of AChE and of NGF. The mice received a daily injection of the compound XVI in a dose of 7 mg/kg. Only in the case of behavioural analysis did they receive a dose of 15 mg/kg/day per os.

Tacrine was administered by intraperitoneal injection in a dose of (0.1 mg/kg/day and 3.5 mg/kg/day) from age 1.5 months for 15 days, while Galantamine was administered by intraperitoneal injection for the same period and from age 6 months. Moreover, it was administered for 4 months from age 2 months per os (3.5 mg/kg/day).

In all the experiments the control mice were age-matched non transgenic mice, age-matched AD11 mice to which saline solution was administered via intraperitoneal injection or water containing the same percentage of ethanol present in the solution of the compound XVI.

Histology and Neurostereology

At the end of the treatment, the mice were anaesthetised with 8 µl/gr of chloral hydrate. The brain was removed and placed in an ice-cold petri dish. The encephalon was fixed in 4% paraformaldehyde in phosphate buffer for 24 hours and then cryoprotected in a solution of 30% sucrose in phosphate buffer.

Coronal brain sections were obtained with a sliding freezing microtome. Serial sections were collected in a solution of 1% paraformaldehyde in phosphate buffer.

To evaluate the effects on morphological alterations, sections were incubated with the following primary antibodies against choline acetyltransferase (Anti-ChAT; Chemicon), amyloid precursor protein APP (Chemicon), the phosphorylated fraction of tau protein (clone AT8; Innogenetics), the N terminus of β-amyloid (Santa Cruz).

Neurostereological quantitative analysis was performed on the basal forebrain and entorhinal cortex using the optical fractionation method (West M. J., Neurobiol Aging 14, 275-285, 1993; Peterson D. A. et al. J Comp Neurol 404, 1-20, 1999; Michel R. P. & Cruz-Orive L. M. J. Microsc. 150, 117-136, 1988).

The density of extracellular deposits of APP was calculated according to the method used by Schenk (Schenk D., Nature 400, 173-177, 1999), in which the percentage of the cortical area occupied by extracellular deposits is calculated with respect to the total area of the entorhinal cortex.

The number of β-amyloid—positive cell clusters was quantified in the caudal portion of the hippocampus using the optical fractionation method.

Object Recognition Test

The efficacy of compound XVI in rescuing the behavioural deficits in AD11 mice was analysed using the object recognition test. The analysis consists of evaluating the ability of discriminating between a new object and a familiar one (Bartus, R T. On neurodegenerative diseases, models, and treatment strategies: lessons learned and lessons forgotten a generation following the cholinergic hypothesis. Exp Neurol 163, 495-529, 2000). AD11 mice show a progressive decrease of this ability of distinguishing new objects from old ones (Capsoni, S, Ugolini, G, Comparini, A, Ruberti, F, Berardi, N & Cattaneo, A. Alzheimer-like neurodegeneration in antinerve growth factor transgenic mice. *Proc Natl Acad Sci USA* 97, 6826-6831, 2000).

Before starting the trial, 6 and 12 month old mice were treated with compound XVI for 15 days in a dose of 15/mg/kg/day per os. The controls were age-matched non transgenic mice and transgenic AD11 mice treated with water and the same percentage of ethanol (2%).

The cognitive deficit was also induced in a group of 2-month non transgenic mice by subcutaneous administration of 0.5 mg/kg of scopolamine, a muscarinic receptor antagonist (Weiss B, Heller A. Methodological problems in evaluating the role of cholinergic mechanisms in behavior. Fed Proc 28, 135-146, 1969). A second group of animals received compound XVI (per os, 15 mg/kg) 20 min. before scopolamine injection. A third group of non transgenic mice was formed by non-treated non transgenic mice.

The efficacy of Galantamine in rescuing the behavioural deficit in AD11 mice was analysed after oral administration of 3.5 mg/kg/day starting from 2 months of age until 6 months of age.

To carry out the experiment, the mice were placed in a box made of Plexiglas (60 cm×60 cm×60 cm). The walls and the floor of the box were covered with opaque, washable material. The box and objects used in this test were also washable. The box and objects were cleaned up between trials to stop build-up of olfactory cues. The mice received 3 sessions of 10 min duration in the empty box to allow them to become familiar with the apparatus. During the test, each mouse was put back in the box and exposed to two identical objects (object A1 and A2, for example 2 cubes 12 cm wide) for 10 minutes. The experimenter measured the total time spent exploring each of the two objects. Then the mouse was returned to its cage. During an interval of 1 minute, 1 hour and 24 hours, the objects were removed from the box and one of the two was replaced by its identical copy (A3), while the other was replaced with a completely new object (object B). After a delay of 1 min., 1 hour and 24 hours the mouse was put back in the box and exposed to the familiar object A3 and to the new object B for 10 min. The objects were placed in the same locations as the previous ones. The experimenter again measured the total time spent exploring each of the two objects. Exploration time is operationally defined as the time during which the mouse directly attended towards the object with its head, at a distance not greater than 2 cm from the object. The discrimination index was calculated using the formula (N−F/N+F), where N is the time spent exploring the new object, and F the time spent exploring the familiar object.

Results (a) Efficacy in Blocking Cholinergic Deficit, Tau Phosphorilation and β-Amyloid Aggregation in Aged AD11 Mice After Oral Administration Neurodegeneration in AD11 mice worsens with age and is fully blown at 15 months of age. At this age, the following can be seen in the brain of AD11 mice: neuronal death, cholinergic deficit (Melchiorre, C, Andrisano, V, Bolognesi, M L, Budriesi, R, Cavalli, A, Cavrini, V, Rosini, M, Tumiatti, V & Recanatini, M. Acetylcholinesterase noncovalent inhibitors based on a polyamine backbone for potential use against Alzheimer's disease. *J Med Chem* 41, 4186-4189, 1998; Selkoe, D J. Alzheimer's disease: genes, proteins, and therapy. *Physiol Rev* 81, 741-766, 2001), presence of extracellular β-amyloid plaques (Inestrosa, N C, Alvarez A, Perez C A, Moreno R D, Vicente M, Linker C, Casanueva O I, Soto C, Garrido J. Acetylcholinesterase accelerates assembly of amyloid-beta-peptides into Alzheimer's fibrils: possible role of the peripheral site of the enzyme. *Neuron* 16, 881-91, 1996), dystrophic neurites and intracellular tangles composed of the hyperphosphorylated form of tau protein.

Figure 9:
FIGS. 9A, 9B, 9C illustrate coronal sections of the basal forebrain of, respectively, non transgenic mice, transgenic mice (AD11) and transgenic mice (AD11) treated with a 2,5-bis-diamine-[1,4]benzoquinonic derivative having a general formula (I)

The compound XVI was administered per os in a dose of 7 mg/kg/day for 1 month to AD11 mice aged 15 months (n=6, n is the number of mice used). The treatment determined an improvement in the number of cholinergic neurons in the basal forebrain (FIG. 9).

Figure 10:
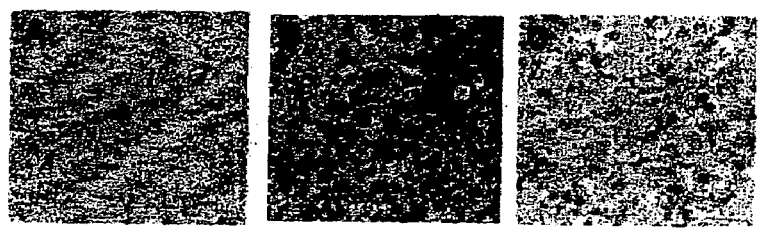
FIGS. 10A, 10B, 10C illustrate coronal sections of the entorhinal cortex of, respectively, non transgenic mice, transgenic mice (AD11), transgenic mice (AD11) treated with a 2,5-bis-diamine-[1,4]benzoquinonic derivative having a general formula (I)

The intracellular accumulation of hyperphosphorylated tau decreased in the mice treated with the compound XVI (FIG. 10C) in comparison with placebo-treated mice (FIG. 10B). The number of the cells containing phosphorylated tau in the somatodendritic compartment was approximately the same as that of age-matched non transgenic mice (FIG. 10A).

Figure 11:
FIGS. 11A, 11B, 11C illustrate sections of the hippocampus of, respectively, non transgenic mice (AD11), transgenic mice (AD11) and transgenic mice (AD11) treated with a 2,5-bis-diamine-[1,4]benzoquinonic derivative having a general formula (I)

The administration of the compound XVI determined a decrease in the number of β-amyloid plaques in AD11 mice (FIG. 11C) in comparison with placebo-treated mice (FIG. 11B). Although the number of plaques did not reach the level that can be observed in age-matched non transgenic mice (FIG. 11A), the morphology of plaques was different from the one observed in placebo-treated mice: the number of cells associated with plaques in mice treated with the compound XVI (FIG. 11C) was lower than that in placebo-treated mice (FIG. 11B).

In conclusion the results described demonstrate that: the compound XVI s active even after oral administration and that the compound XVI is able to improve neurodegeneration also in aged mice in which the pathology is fully blown and in an advanced stage.

Figure 12:
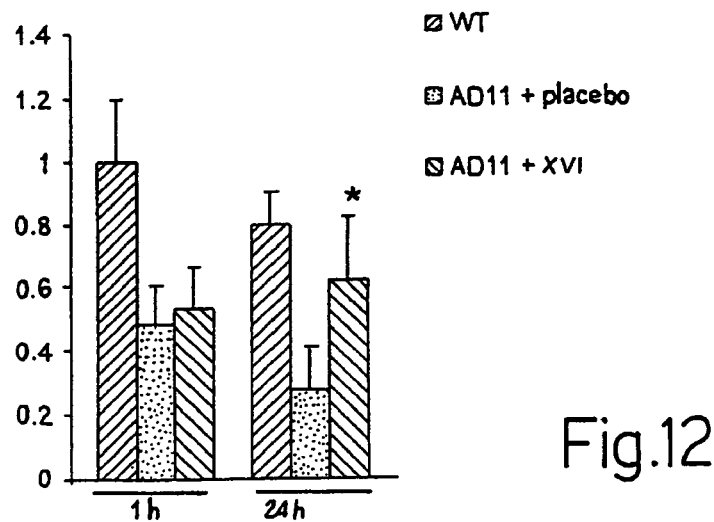
Figure 13:
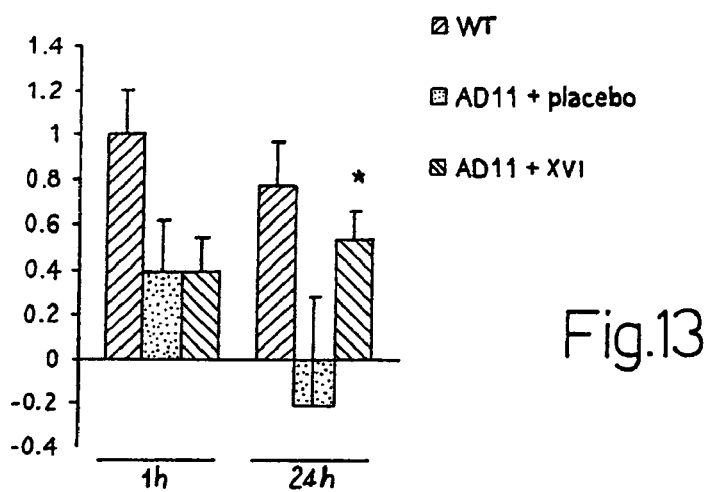

(b) Effects of the Compound XVI on Behavioural Deficits in AD11 Mice and in Mice Treated with Scopolamine The efficacy of the compound XVI in treating behavioural deficit in AD11 mice was analysed using the object recognition test. The analysis consists of the evaluation of the ability to discriminate between new and familiar objects (Bartus, R T. On neurodegenerative diseases, models, and treatment strategies: lessons learned and lessons forgotten a generation following the cholinergic hypothesis. *Exp Neurol* 163, 495-529, 2000). AD11 mice show a progressive decrease in this ability to distinguish new objects from those already explored (Selkoe, D J. Alzheimer's disease: genes, proteins, and therapy. *Physiol Rev* 81, 741-766, 2001). The administration of the compound XVI (15 mg/kg/day per os) allowed an improvement of the deficit in AD11 mice at 6 months (n=10, FIG. 12) and 12 months (n=8; FIG. 13) of age.

Figure 14:
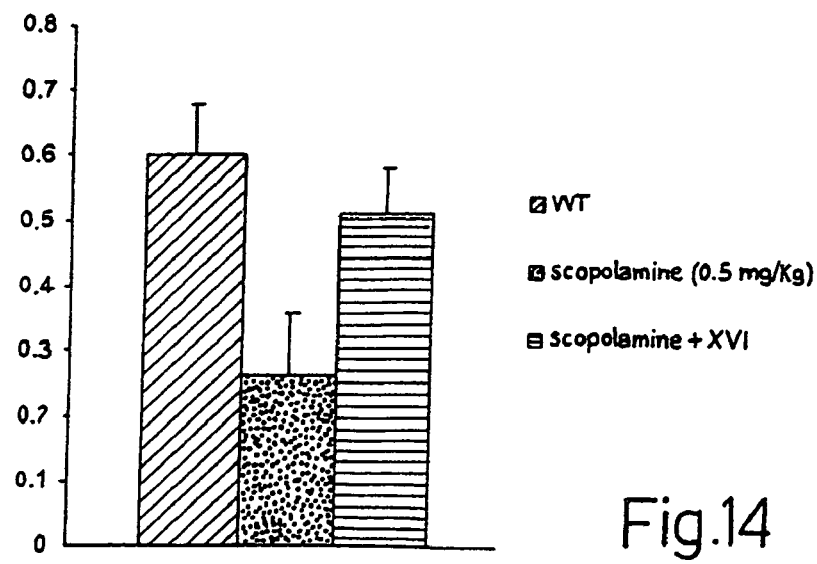

The same test was applied to non transgenic mice treated with the compound XVI 20 minutes before the administration of scopolamine. The mice treated with the compound XVI did not show any signs of amnesia and were able to distinguish the familiar objects from the new ones (FIG. 14).

In conclusion, the compound XVI is able to ameliorate the cognitive deficit determined by NGF deprivation in transgenic mice and by administering scopolamine in non transgenic mice.

(c) Effects of the Administration of the Compound XVI to AD11 Mice Compared with the Effects of other AChE Inhibitors The compound XVI, Galantamine and Tacrine were administered daily to AD11 mice. The drugs were administered per os (compound XVI and Galantamine) or via intraperitoneal injection (compound XVI, Galantamine and Tacrine). They were administered starting from 1.5 months of age until 2 months of age. Treatment with the compound XVI and with Galantamine prevented the decrease of the number of cholinergic neurons in the basal forebrain, while Tacrine aggravated the cholinergic deficit (FIG. 15)

The compound XVI, Galantamine and Caproctamine were also administered to AD11 mice from 6 months of age for 15 days. While the compound XVI and Galantamine were able to rescue the cholinergic deficit in the basal forebrain, Caproctamine had no effect on the number of cholinergic neurons (FIG. 16). After treatment with the compound XVI for 15 days, starting at 1.5 months of age or 6 months of age, the compound XVI reduced the number of neurons labelled with antibodies against phospho-tau (FIGS. 17 and 18). Galantamine (FIGS. 17 and 18) and Caproctamine (FIG. 18) were ineffective.

In 6 month-old AD11 mice, the administration of the compound XVI and Galantamine reduced the extracellular deposition of APP, while Caproctamine was ineffective (FIG. 19).

The treatment with the compound XVI, starting at 6 months of age, was able to reduce the number of cells accumulating β-amyloid protein in the hippocampus of AD11 mice. The same result is obtained using Galantamine, while Caproctamine was ineffective (FIG. 20).

The administration of the compound XVI for 2 weeks from 6 months of age determined a marked amelioration of the behavioural deficit, as occurred also with Galantamine (FIG. 21)

In conclusion, the compound XVI is as effective as Galantamine, but superior to it in reverting the aspect of neurodegeneration linked with tau hyperphosphorylation. Caproctamine was ineffective against all aspects of Alzheimer neurodegeneration. Note also that in the enclosed figures the data marked "*" present P<0.05.

EXAMPLE 56

The antioxidant power of XVI was tested, expressed as the ability to capture oxygen radicals, using the kit of Randox Laboratories® Ltd (UK) (Total antioxidant status) [Rice-Evans C. and Miller N. J. Total antioxidant status in plasma and body fluids, Methods Enzymol. 234 (1994) 279-293], after suitable experimental modification.

The method used to assess the ability to neutralise free radicals is a colorimetric method. It is based on the reactivity of a peroxidase compound, methmyoglobin (6.1 μM) (HXFe$^{3+}$) which, in the presence of hydrogen peroxide (250 μM) in an aqueous buffer with physiological pH, stimulates the formation of oxygen radicals, which it complexes in the form of ferrimyoglobin (*X—[Fe$^{4+}$=O]). Ferrimyoglobin subtracts an electron from a cation (ABTS®) (2,2'-azino-di-[3-ethylbenzthiazoline sulphonate]) (610 μM), returning to a methmyoglobin and transforming ABTS® into coloured radical, detectable at 600 nm.

The capturing of free oxygen radicals by an antioxidant present in a solution reduces the formation of the coloured species and the corresponding absorbance to 600 nm at fixed times.

As reference antioxidant, able to inhibit the chromogenic reaction in a manner depending on concentration, a water-soluble derivative of Vitamin E was used, Trolox (6-hydroxy-2,5,7,8-tetramethylchroman-2-carboxylic acid).

The white is composed of phosphate buffer (80 mM, pH 7.4) methmyoglobin and ABTS® incubated at 37° C., the reference contains in addition Trolox while the sample contains in addition the compound XVI. The substratum $H_2O_2$ was added in each test and the absorbance was read at 600 nm at fixed times ($t_0$ and after 3 min.). The percentage colour loss of the white can be used as an indication of the antioxidant activity of the sample tested.

% inhibition=$\Delta Abs_{white}$−$\Delta Abs_{test}$/$\Delta Abs_{white}$×100

The following data were obtained:

|  | concentration [μM] | % inhibition* |
|---|---|---|
| Trolox | 27 | 57.6 ± 0.9 |
| XVI | 170 | 44.1 ± 3.7 |

*Mean of two independent measurements, repeated in triplicate

The modification of the method shown concerns the addition of human serum albumin (25 μM) in the sample containing the compound XVI to assist its solubilisation and its respective white.

In the system described, the compound XVI demonstrated an antioxidant activity (capture of free radicals) because it inhibited the formation of the coloured radical species. The antioxidant power of the compound XVI is about 6 times lower than Trolox. However it must be stressed that the compound XVI was tested in the oxidated quinonic form, which in vivo in contact with the enzymatic reducing systems, can be transformed into the more active hydroquinonic reduced form.

The invention claimed is:

1. 2,5-bis-diamine-[1,4]benzoquinonie derivative having a general formula (I):

(I)

wherein $R_1$ represents a substituent chosen from the group consisting of:
a hydrogen,
a saturated or unsaturated, linear or ramified alkylic group of from one to five carbon atoms, and
a substituent having an inductive electron withdrawing effect;
$R_2$ and $R_3$ each independently of the other, represent a hydrogen or a saturated or unsaturated, linear or ramified alkylic group presenting from one to five carbon atoms;
$R_4$ and $R_5$, each independently of the other, represent a substituent chosen from the group consisting of:
hydrogen,
a saturated or unsaturated, linear or ramified alkylic group presenting from one to five carbon atoms,
OMe, and
SMe;
X represents a radical —HC=CH—;
T represents a saturated linear alkyl presenting from one to four carbon atoms;
Z represents a saturated or unsaturated, linear or ramified alkyl presenting from two to thirteen carbon atoms.

2. 2,5-bis-diamine-[1,4]benzoquinonie derivative having a general formula (I) according to claim 1, wherein $R_1$ represents a substituent chosen from the group consisting of:
a hydrogen, a halogen, $NO_2$, and an alkoxy group.

3. 2,5-bis-diamine-[1,4]benzoquinonie derivative having a general formula (I) according to claim 1, wherein $R_1$ represents a substituent chosen from the group consisting of:
a hydrogen,
a halogen,
$NO_2$, and
MeO;
$R_2$ and $R_3$, each independently of the other, represent a hydrogen or a saturated or unsaturated, linear or ramified alkylic group presenting from one to four carbon atoms;
$R_4$ and $R_5$, each independently of the other, represent a substituent chosen from the group consisting of:
hydrogen,
a saturated or unsaturated, linear or ramified alkylic group of from one to five carbon atoms,
T represents a saturated linear alkyl presenting from one to three carbon atoms;
Z represents a saturated or unsaturated, linear or ramified alkyl presenting from two to twelve carbon atoms.

4. 2,5-bis-diamine-[1,4]benzoquinonie derivative having a general formula (I) according to claim 1, wherein $R_1$ represents a substituent chosen from the group consisting of:
a hydrogen,
a halogen,
MeO;
$R_2$ and $R_3$, each independently of the other, represent a hydrogen or a saturated or unsaturated, linear or ramified alkylic group presenting from one to two carbon atoms;
$R_4$ and $R_5$, each independently of the other, represent a substituent chosen from the group consisting of:
hydrogen,
a saturated or unsaturated, linear or ramified alkylic group of from one to four carbon atoms,
T represents the radical —$CH_2$—; and
Z represents a saturated or unsaturated, linear or ramified alkyl presenting from two to seven carbon atoms.

5. 2,5-bis-diamine-[1,4]benzoquinonie derivative having a general formula (I) according to claim 3,
$R_3$ represents a hydrogen;
$R_4$ and $R_5$, each independently of the other, represent a substituent chosen from the group consisting of:
hydrogen,
a saturated or unsaturated, linear or ramified alkylic group of from one to five carbon atoms,
a ramified alkylic group of from three to four carbon atoms,
Z represents a saturated linear alkyl presenting from two to seven carbon atoms.

6. 2,5-bis-diamine-[1,4]benzoquinonie derivative having a general formula (I) according to claim 1, wherein $R_1$ is in position 2 with respect to T.

7. 2,5-bis-diamine-[1,4]benzoquinonie derivative having a general formula (I) according to claim 1, wherein Z represents a saturated linear alkylic group presenting from two to seven carbon atoms.

8. 2,5-Bis-{6-[ethyl-(2-methoxy-benzyl)-amino]-hexylamino}-[1,4]benzoquinone (XVI).

9. 2,5-Bis-{3-[ethyl-(2-methoxy-benzyl)-amino]-propylamino}-[1,4]benzoquinone (XII).

10. 2,5-Bis-[6-(benzyl-ethyl-amino)-hexylamino]-[1,4]benzoquinone (XVII).

11. 2,5-Bis-{6-[ethyl-(3-methoxy-benzyl)-amino]-hexylamino}-[1,4]benzoquinone (XXXIII).

12. 2,5-Bis-{6-[ethyl-(4-methoxy-benzyl)-amino]-hexylamino}-[1,4]benzoquinone (XXXVII).

13. 2,5-Bis-{2-[ethyl-(2-methoxy-benzyl)-amino]-ethylamino}-[1,4]benzoquinone (XLV).

14. 2,5-Bis-{7-[ethyl-(2-methoxy-benzyl)-amino]-heptylamino}-[1,4]benzoquinone (IL).

15. 2,5-Bis-{6-[(2-methoxy-benzyl)-methylamino]-hexylamino}-[1,4]-benzoquinone (LIV).

16. 2,5-Bis-{6-[ethyl-(2-methoxy-benzyl)-amino]-hexylamino}-3,6-dimethyl-[1,4]-benzoquinone (LV).

17. 2,5-Bis-[6-(2-methoxy-benzylamino)-hexylamino]-[1,4]-benzoquinone (LI).

18. 2,5-Bis-[6-(ethyl-furan-2-ilmethyl-amino)-hexylamino]-[1,4]benzoquinone (XLI).

19. 2,5-Bis-{6-[ethyl-(2-nitro-benzyl)-amino]-hexylamino}-[1,4]benzoquinone (XXIX).

20. 2,5-Bis-{6-[ethyl-(2-chloro-benzyl)-amino]-hexylamino}-[1,4]benzoquinone (XVIII).

21. Pharmaceutical preparation comprising a 2,5-bis-diamine-[1,4]benzoquinonie derivative according to claim 1, and a pharmaceutically acceptable excipient and/or diluant.

22. 2,5-bis-diamine-[1,4]benzoquinone derivative having a general formula (I) according to claim 1, wherein $R_1$ represents an alkoxy group.

23. 2,5-bis-diamine-[1,4]benzoquinone derivative having a general formula (I) according to claim 1, wherein $R_1$ represents MeO.

24. 2,5-bis-diamine-[1,4]benzoquinone derivative having a general formula (I) according to claim 1, wherein $R_3$ is a hydrogen and Z is a saturated linear alkyl having a number of carbon atoms chosen in the group consisting of: two and six.

25. 2,5-bis-diamine-[1,4]benzoquinone derivative having a general formula (I) according to claim 1, wherein Z is ethyl.

\* \* \* \* \*